(12) United States Patent
Altobelli et al.

(10) Patent No.: US 11,173,056 B2
(45) Date of Patent: Nov. 16, 2021

(54) DYNAMIC SUPPORT APPARATUS

(71) Applicant: DEKA Products Limited Partnership, Manchester, NH (US)

(72) Inventors: David E. Altobelli, Hollis, NH (US); N. Christopher Perry, Manchester, NH (US)

(73) Assignee: DEKA PRODUCTS LIMITED PARTNERSHIP, Manchester, NH (US)

( * ) Notice: Subject to any disclaimer, the term of this patent is extended or adjusted under 35 U.S.C. 154(b) by 0 days.

(21) Appl. No.: 14/524,790

(22) Filed: Oct. 27, 2014

(65) Prior Publication Data

US 2015/0045910 A1    Feb. 12, 2015

Related U.S. Application Data

(63) Continuation of application No. 12/026,971, filed on Feb. 6, 2008, now Pat. No. 8,870,970.

(Continued)

(51) Int. Cl.
*A61F 2/78* (2006.01)
*A61F 2/50* (2006.01)
(Continued)

(52) U.S. Cl.
CPC ............ *A61F 2/7843* (2013.01); *A61F 5/012* (2013.01); *B29C 33/3842* (2013.01); *A61F 2/602* (2013.01);
(Continued)

(58) Field of Classification Search
CPC .................................................... A61F 2/7843
See application file for complete search history.

(56) References Cited

U.S. PATENT DOCUMENTS

| 4,841,773 A | 6/1989 | Stewart |
| 5,080,682 A | 1/1992 | Schectman |

(Continued)

FOREIGN PATENT DOCUMENTS

| FR | 484359 A | 10/1917 |
| WO | 02/00158 A2 | 1/2002 |
| WO | 2009/155595 A2 | 12/2009 |

OTHER PUBLICATIONS

Invitation to Pay Additional Fees and, Where Applicable, Protest Fee including Partial Search Report from corresponding International Appln. No. PCT/US2016/043864 dated Nov. 11, 2016 (7 pages).

(Continued)

*Primary Examiner* — Jacqueline Woznicki
(74) *Attorney, Agent, or Firm* — McCormick, Paulding & Huber PLLC

(57) ABSTRACT

A dynamic support apparatus having a frame, a dynamic interface, a temperature control mechanism, and a control system. The dynamic interface is capable of changing its geometry and is disposed on the top surface of the frame. The control system is operably connected to the dynamic interface and controls the changing geometry of the dynamic interface. There is also a temperature control mechanism disposed on the top surface of the frame for maintaining a comfortable temperature and moisture environment between the apparatus and the user's body.

11 Claims, 18 Drawing Sheets

Related U.S. Application Data

(60) Provisional application No. 60/899,835, filed on Feb. 6, 2007.

(51) Int. Cl.

| | | |
|---|---|---|
| *A61F 2/76* | (2006.01) | |
| *A61F 2/70* | (2006.01) | |
| *A61F 5/01* | (2006.01) | |
| *B29C 33/38* | (2006.01) | |
| *A61F 2/60* | (2006.01) | |
| *A61F 7/00* | (2006.01) | |
| *B29L 31/00* | (2006.01) | |

(52) U.S. Cl.
CPC ........... *A61F 2/70* (2013.01); *A61F 2002/501* (2013.01); *A61F 2002/5012* (2013.01); *A61F 2002/5032* (2013.01); *A61F 2002/7615* (2013.01); *A61F 2002/7887* (2013.01); *A61F 2007/006* (2013.01); *B29L 2031/753* (2013.01)

(56) References Cited

U.S. PATENT DOCUMENTS

| | | |
|---|---|---|
| 5,252,102 A | 10/1993 | Singer et al. |
| 5,336,269 A | 8/1994 | Smits |
| 5,617,595 A | 4/1997 | Landi et al. |
| 5,748,845 A | 5/1998 | Labun et al. |
| 5,881,609 A | 3/1999 | Palmer |
| 6,177,034 B1 | 1/2001 | Ferrone |
| 6,685,661 B2 | 2/2004 | Peled |
| 6,993,849 B1 | 2/2006 | Campbell et al. |
| 7,186,270 B2 | 3/2007 | Elkins |
| 8,430,578 B1 | 4/2013 | Theriault |
| 8,453,340 B2 | 6/2013 | van der Merwe et al. |
| 8,821,587 B2 | 9/2014 | Lanier et al. |
| 9,114,028 B2 | 8/2015 | Langenfeld et al. |
| 10,092,423 B2 | 10/2018 | Goldfarb et al. |
| 2002/0099450 A1* | 7/2002 | Dean, Jr. .................. A61F 2/76 623/26 |
| 2003/0018388 A1 | 1/2003 | Comer |
| 2003/0078674 A1* | 4/2003 | Phillips .................. A61F 2/7843 623/37 |
| 2004/0267379 A1 | 12/2004 | Pasolini |
| 2005/0177952 A1 | 8/2005 | Wilkinson et al. |
| 2005/0256507 A1 | 11/2005 | Long et al. |
| 2006/0135883 A1 | 6/2006 | Jonsson et al. |
| 2006/0155386 A1 | 7/2006 | Wells et al. |
| 2008/0078033 A1 | 4/2008 | Wyatt et al. |
| 2008/0200994 A1 | 8/2008 | Colgate et al. |
| 2008/0262636 A1 | 10/2008 | Puchhammer |
| 2010/0036507 A1 | 2/2010 | Gow |
| 2011/0082566 A1 | 4/2011 | Herr et al. |

OTHER PUBLICATIONS

Lee et al., "A Composite Discrete/Continuous Control of Robot Manipulators", Apr. 1991, Carnegie Mellon University: The Robotics Institute, Pittsburg, PA, pp. 1-21.

* cited by examiner

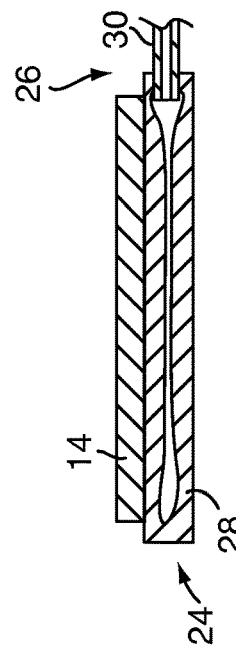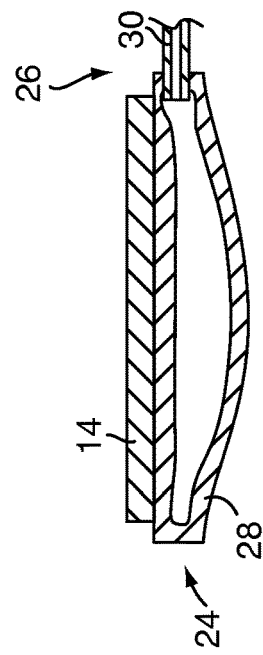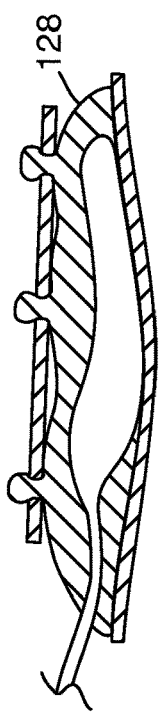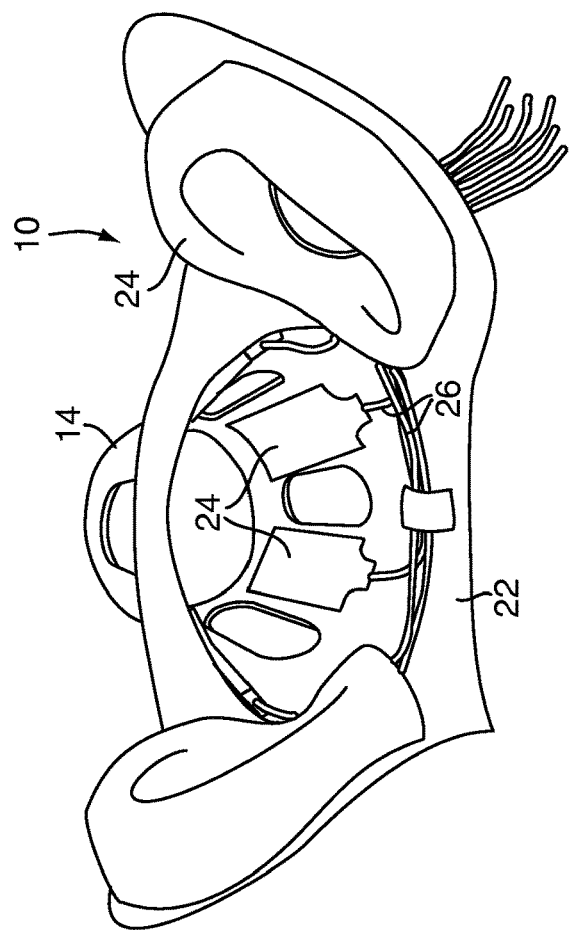

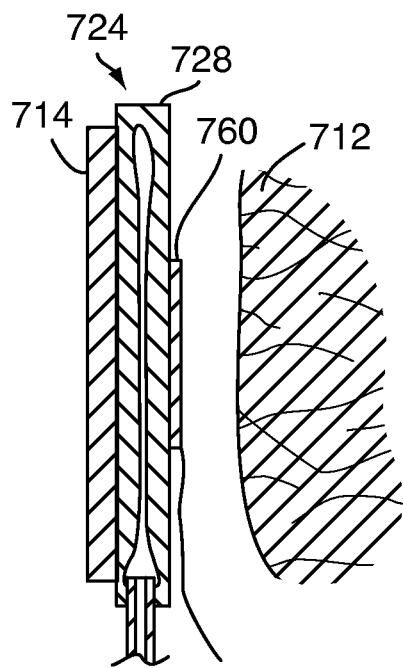
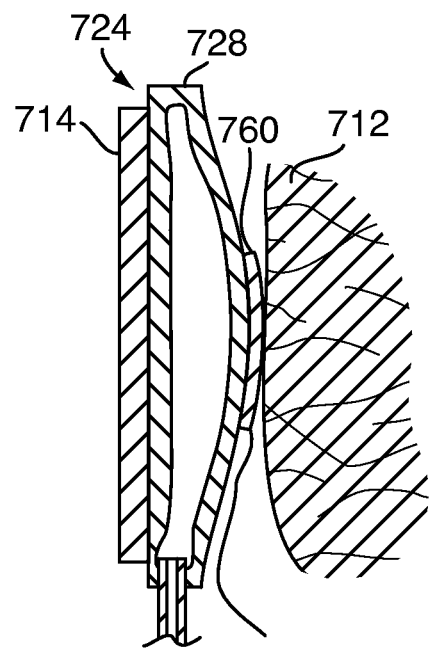
FIG. 23   FIG. 24
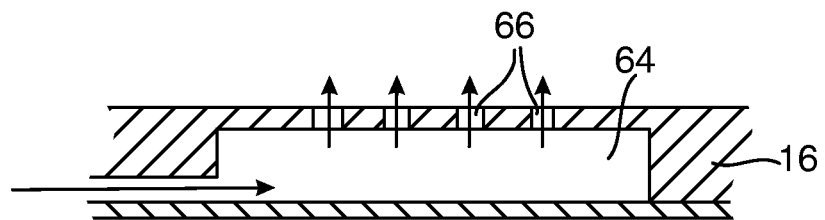
FIG. 25

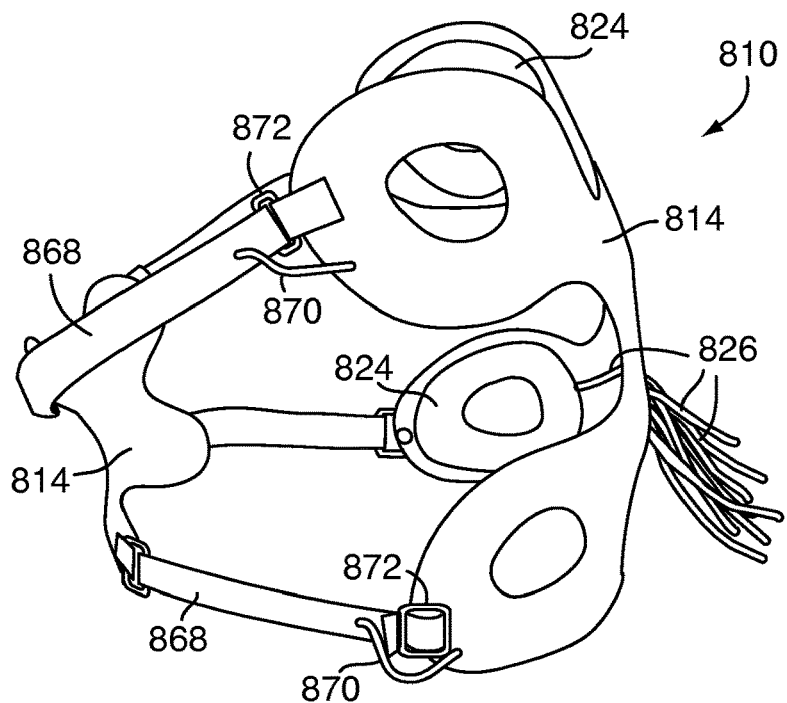
FIG. 28
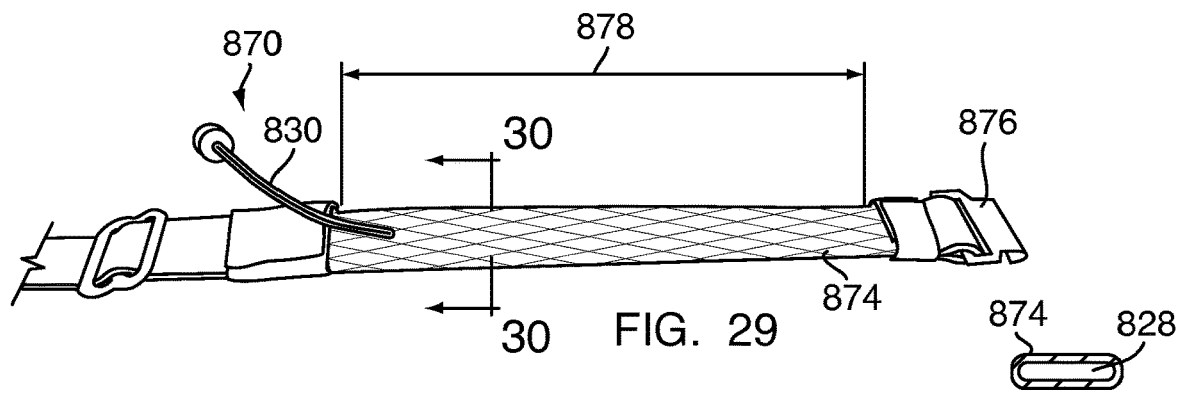
FIG. 29
FIG. 30
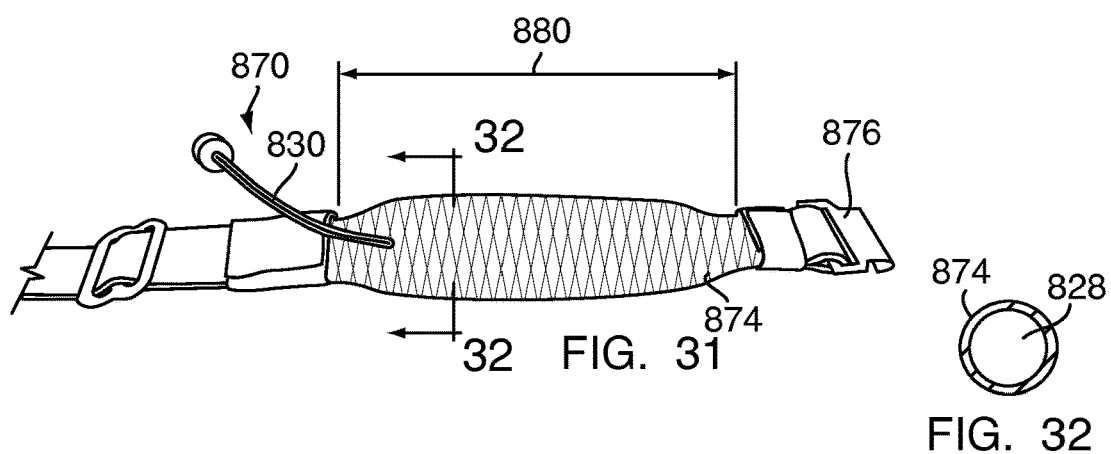
FIG. 31
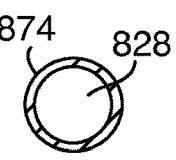
FIG. 32

DYNAMIC SUPPORT APPARATUS

CROSS REFERENCE TO RELATED APPLICATIONS

This application is a continuation of U.S. patent application Ser. No. 12/026,971, filed Feb. 6, 2008, which claims priority to U.S. Provisional Patent Application Ser. No. 60/899,835, filed Feb. 6, 2007, entitled "Dynamic Support Apparatus", each of which is hereby incorporated by reference in its entirety.

STATEMENT OF GOVERNMENT INTEREST

This invention was made with Government support under Contract Number W911 NF-06-C-001 awarded by the U.S. Army RDECOM ACQ CTR. The Government has certain rights in the invention.

TECHNICAL FIELD

The present invention relates to support apparatuses and more specifically to dynamic support apparatuses.

BACKGROUND OF THE INVENTION

This support apparatus may be used for upper-limb and lower-limb prosthetic devices, or any device with interaction with the body, but for exemplary purposes, the present apparatus will be described in the context of prostheses for upper-limb amputees.

Accordingly, there is a need for a dynamic support apparatus that accommodates users' needs in the interaction with the user. A device that can, in addition to other features, include changing geometry in response to residuum morphing to maintain a secure, comfortable fit with the user's body, and/or maintain a comfortable temperature and moisture environment between the support apparatus and the user's body is desired.

SUMMARY OF THE INVENTION

In accordance with one aspect of the present invention, the dynamic support apparatus includes a frame, a dynamic interface capable of changing its geometry, and a control system. The dynamic interface is disposed on a surface of the frame and has at least one actuator. The control system is operably connected to the dynamic interface by at least one connector.

In accordance with another aspect of the invention, the at least one actuator is a bladder capable of changing geometry when filled with a gas or a liquid. The bladder is capable of changing geometry in a specific direction. In accordance with another aspect of the present invention, the control system is a pneumatic system. A manifold may control the distribution of air to the at least one bladder.

In accordance with another aspect of the present invention, at least one sensor provides information on the stability and fit of the support apparatus to the control system. In accordance with a further aspect of the present invention, the at least one sensor is a pressure transducer. In accordance with another aspect of the present invention, the control system maintains a constant pressure measured by the pressure transducer. In accordance with a further aspect of the present invention, the control system actuates a change in geometry of the dynamic interface based on the information provided by the at least one sensor.

In accordance with another aspect of the present invention, the at least one actuator and the at least one connector are molded inside the dynamic interface. In accordance with a further aspect of the present invention, the at least one actuator and the at least one connector are integrally molded as part of the dynamic interface.

In accordance with another aspect of the present invention, the frame has an opening to allow expansion of the dynamic support apparatus. In a further aspect of the present invention, the dynamic support has a securing mechanism to preclude expansion thereof.

In accordance with another aspect of the present invention, the dynamic support apparatus includes a frame, a dynamic interface capable of changing its geometry, a control system, and a temperature control mechanism. The dynamic interface is disposed on the top surface of the frame and has at least one actuator. The control system is operably connected to the dynamic interface to control the changing geometry of the dynamic interface. The temperature control mechanism is disposed on the top surface of the frame for maintaining a comfortable temperature and moisture environment between the apparatus and the user's body. In accordance with a further aspect of the present invention, the temperature control mechanism has at least one aperture formed within the frame. In accordance with another aspect of the present invention, the temperature control mechanism has at least one duct included in the dynamic interface. In accordance with a further aspect of the present invention, the temperature control mechanism has at least one orifice formed within the dynamic interface. In accordance with a further aspect of the present invention, the temperature control mechanism has at least one temperature sensor.

In another aspect, the present invention relates to a method of fabricating a dynamic interface of a dynamic support apparatus. The method comprises scanning a contour of a residuum to define an outline of an interface between the frame and the residuum. The method also comprises flattening the outline to form a template. The method further comprises machining the template into a mold. The method additionally comprises pouring a material for the dynamic interface to half a desired final thickness of the dynamic interface to create a first interface layer. The method also comprises placing actuators and connectors on the first interface layer. The method further comprises pouring the material for the dynamic interface to the desired final thickness of the dynamic interface to create a second interface layer. The method additionally comprises removing the resulting dynamic interface from the mold.

These aspects of the invention are not meant to be exclusive and other features, aspects, and advantages of the present invention will be readily apparent to those of ordinary skill in the art when read in conjunction with the appended claims and accompanying drawings.

BRIEF DESCRIPTION OF THE DRAWINGS

These and other features and advantages of the present invention will be better understood by reading the following detailed description, taken together with the drawings wherein:

FIG. 3 is an internal view of the embodiment of the dynamic support apparatus of FIGS. 1 and 2;

FIG. 4 is a cross-sectional view of one embodiment of an actuator of the dynamic support apparatus in an inactuated state;

FIG. 5 is a cross-sectional view of the actuator of FIG. 4 of the dynamic support apparatus in an actuated state;

FIG. 6 is a cross-sectional view of another embodiment of an actuator of the dynamic support apparatus in an inactuated state;

FIG. 7 is a cross-sectional view of the actuator of FIG. 6 of the dynamic support apparatus in an actuated state;

FIG. 23 is a cross-sectional view of an un-actuated actuator and sensor unit;

FIG. 24 is the cross-sectional view of FIG. 23 with the actuator actuated;

FIG. 25 is a cross-sectional view of one embodiment of a temperature control system of a dynamic support apparatus;

FIG. 28 is a structural view of the dynamic support apparatus of FIGS. 26 and 27;

FIG. 29 is a perspective view of one embodiment of an un-actuated active strap of a dynamic support apparatus;

FIG. 30 is a cross-sectional view of the active strap of FIG. 29;

FIG. 31 is a perspective view of the active strap of FIGS. 29 and 30 when actuated;

FIG. 32 is a cross sectional view of the actuated active strap of FIG. 31;

DETAILED DESCRIPTION OF THE PREFERRED EMBODIMENTS

Figure 1:
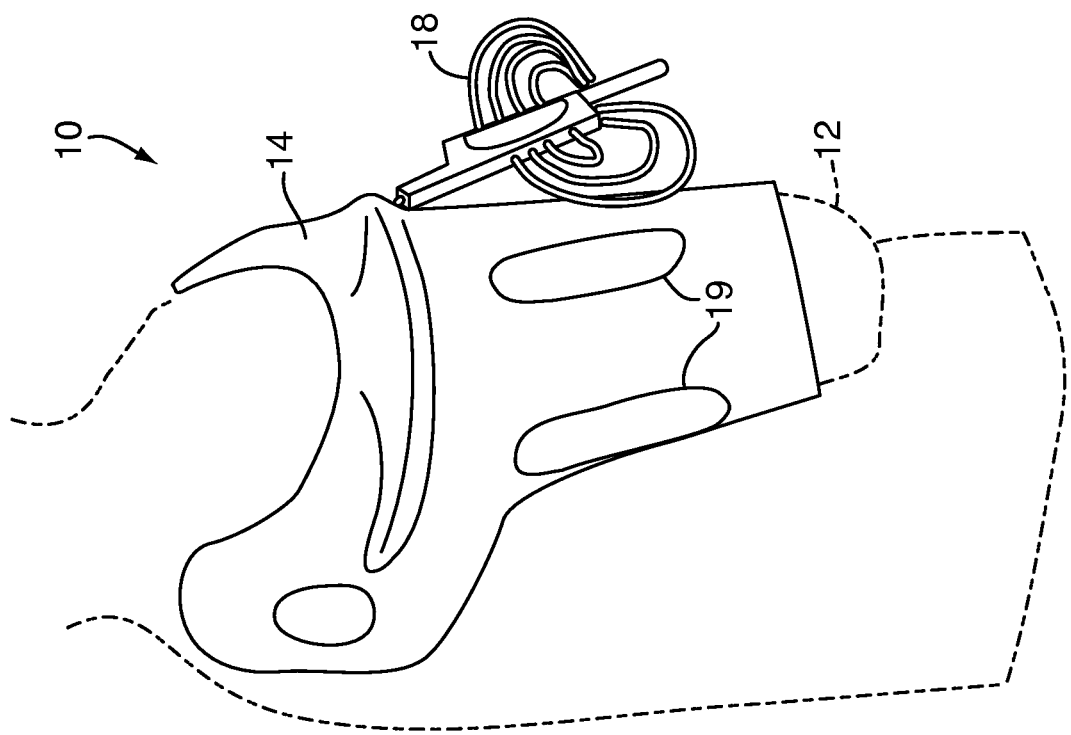
FIG. 1 is a perspective view of one embodiment of a dynamic support apparatus.

For exemplary purposes, the support apparatus will be described in the embodiment of a support apparatus 10 for an upper-limb trans-humeral (TH) prosthesis, as seen in FIG. 1.

Figure 2:
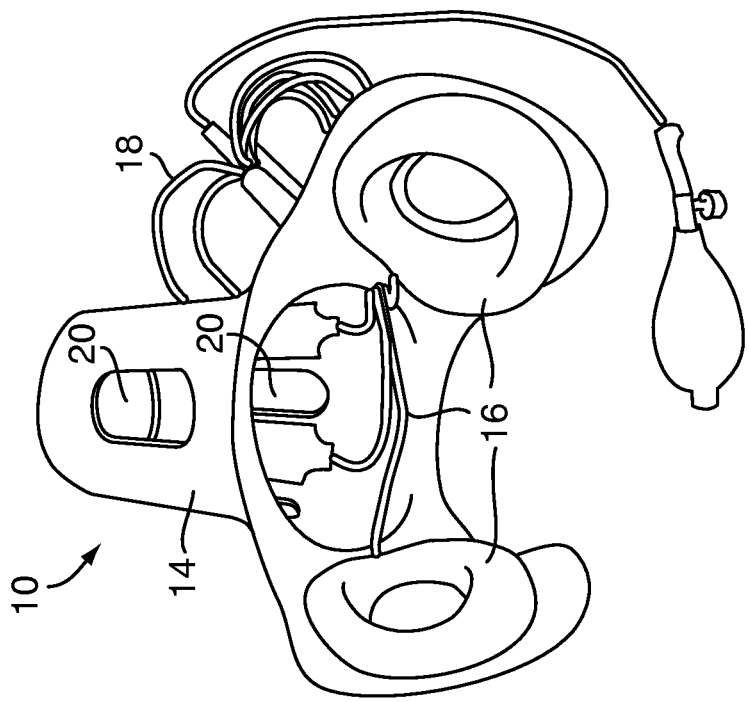
FIG. 2 is a top view of the embodiment of the dynamic support apparatus of FIG. 1.

Referring to FIG. 2, the support apparatus 10, which is utilized to removably adhere a prosthesis to an upper-limb residuum 12 (FIG. 1), includes a frame 14, a dynamic interface 16, a control system 18, and a temperature control mechanism 19. The frame may be made of high tech composite material such as carbon fiber.

In one embodiment, the frame 14 may be open and have a plurality of apertures 20. The structural members of the frame of this embodiment may be strategically placed to maximize the openness of the apparatus. Additionally, the plurality of apertures 20 may be the temperature control mechanism or function as a part of the temperature control mechanism.

Referring to FIG. 3, the dynamic interface 16 is disposed on a top surface 22 of the frame closest to the upper-limb residuum 12. The dynamic interface 16 includes one or more actuators 24 of various shapes and sizes that can be positioned either longitudinally and/or circumferentially along the frame 14. The actuators 24 are capable of changing their geometry and volume to account for morphing in the residuum 12. The actuators 24 may be bladders filled with air, incompressible gas or incompressible liquid, electroactive polymers (EAPs), or other types of actuators capable of changing their geometry. The dynamic interface also includes one or more connectors 26 that connect the actuator(s) 24 to the control system 18. The connector(s) may be fluid paths, tubes, wires, or other similar channels.

Referring to FIGS. 4 and 5, in an embodiment having bladders 28 for actuators 24 and fluid path connectors 30 for connectors 26, the bladder 28 will change geometry from an inactuated position shown in FIG. 4 to the actuated position shown in FIG. 5 when filled with air. Although the bladder 28 is shown with a substantially uniform cross section in FIGS. 4 and 5, the same functionality may be obtained from the bladder 128 having a non-uniform cross-section shown inactuated in FIG. 6 and actuated in FIG. 7, wherein the like numerals represent the like elements.

Figure 10:
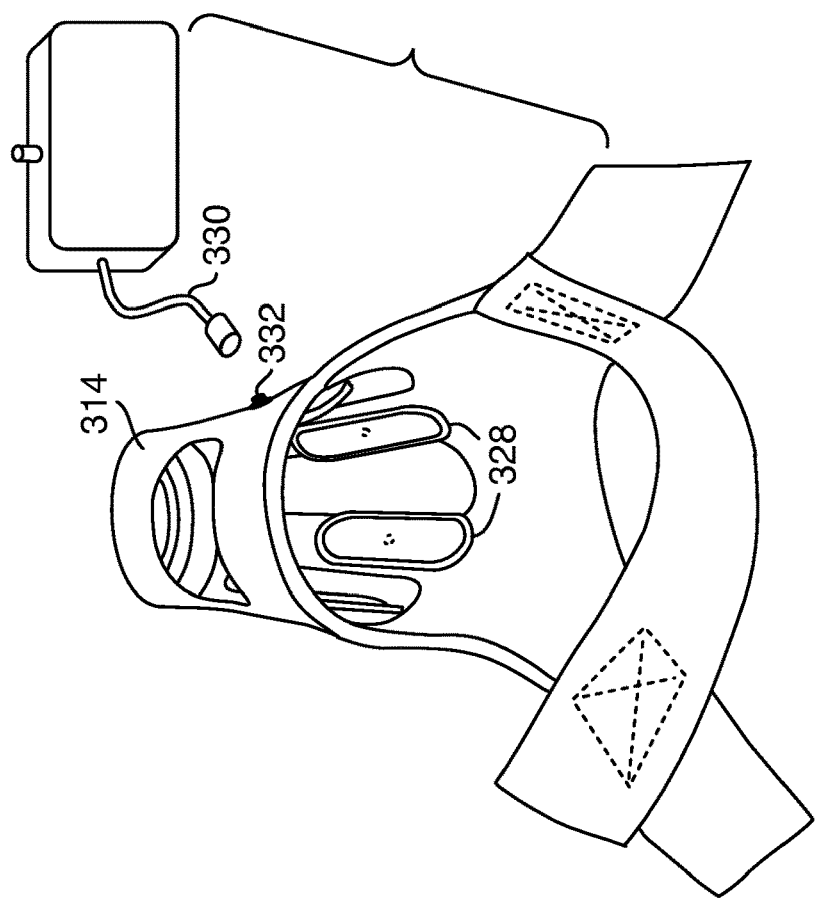
FIG. 10 is a perspective view of a dynamic support apparatus with the actuators of FIG. 9 installed.
Figure 8:
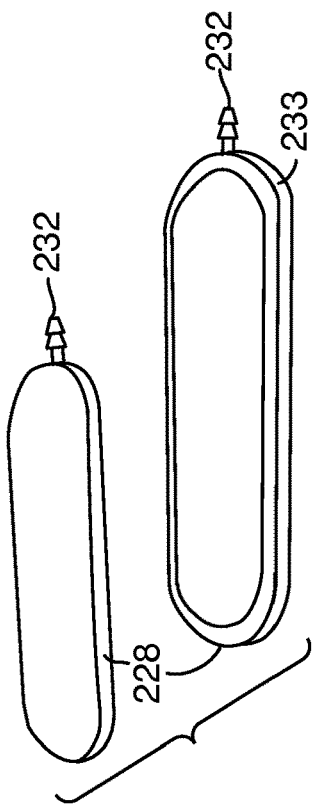
FIG. 8 is a perspective view showing the top and bottom of one embodiment of an actuator of the dynamic support apparatus.
Figure 9:
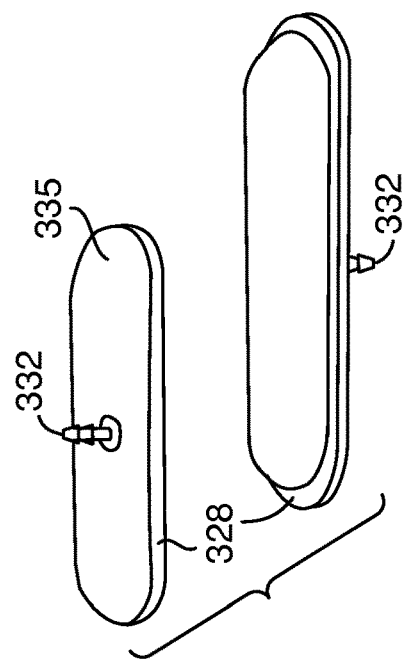
FIG. 9 is a perspective view showing the top and bottom of another embodiment of an actuator of the dynamic support apparatus.

Referring to FIG. 8, in a further embodiment, the bladders 228 may have bladder inlets 232 to facilitate the connection of the fluid path connectors 30. The bladder inlets 232 may be located at any position on a periphery 233 of each bladder 228 to accommodate the desired fluid path connector routing configuration. Referring to FIG. 9, an alternative embodiment positions the bladder inlet 332 on a body 335 of the bladder 328. In this embodiment, as seen in FIG. 10, the bladder inlet 332 may pass through the frame 314 to facilitate connection to the fluid path connectors 330.

In one embodiment, the frame has an outer shell and an inner shell. Here, the dynamic interface may be disposed between the outer shell and the inner shell. The inner shell may also have apertures to dictate the shape the actuator(s). For example, if the actuator(s) are bladders, the inner shell apertures would dictate the shape of the bladder as it is inflated.

Figure 11:
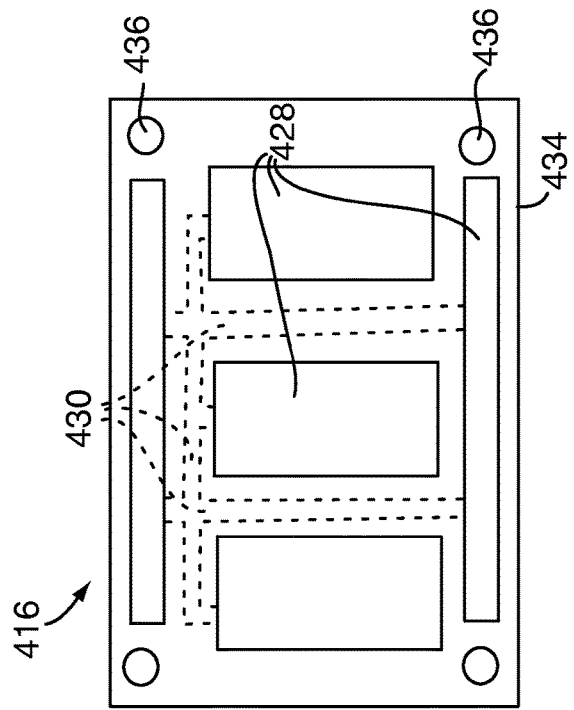
FIG. 11 is a top view of one embodiment of the dynamic interface of a dynamic support apparatus.
Figure 12:
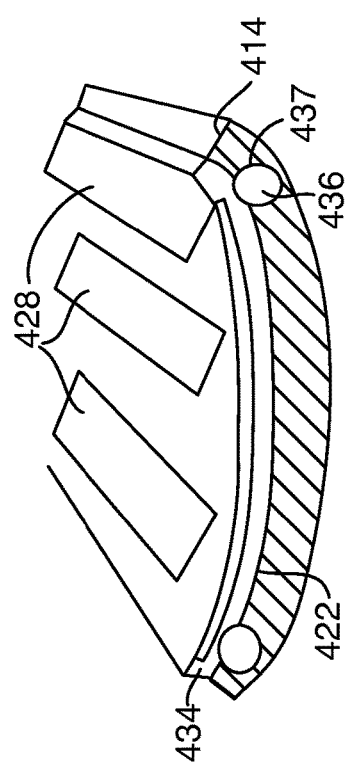
FIG. 12 is a side view of the dynamic interface of FIG. 11 with respect to the frame of an embodiment of a dynamic interface.

In another alternative embodiment, referring to FIGS. 11 and 12, the dynamic interface 416 is a single integrated layer 434 disposed on the top surface 422 of the frame 414. For example, in an embodiment having bladders 428 with fluid path connectors 430, the bladders 428 and fluid paths connectors 430 are embedded into a single layer of material that is placed on top of the frame 414. The single integrated layer 434 may be made of any material that allows for morphable chambers that can house or act as actuators of variable geometry. Such material may be silicon or rapid prototype molding material covered with a layer of silicon. The single integrated layer 434 may also have nodules 436 to attach to the frame 414 having corresponding apertures 437 for the nodules 436. In some embodiments, the nodules 436 are protrusions. The nodules 436 do not have to be round bumps as depicted in one embodiment of the apparatus.

Figure 13:
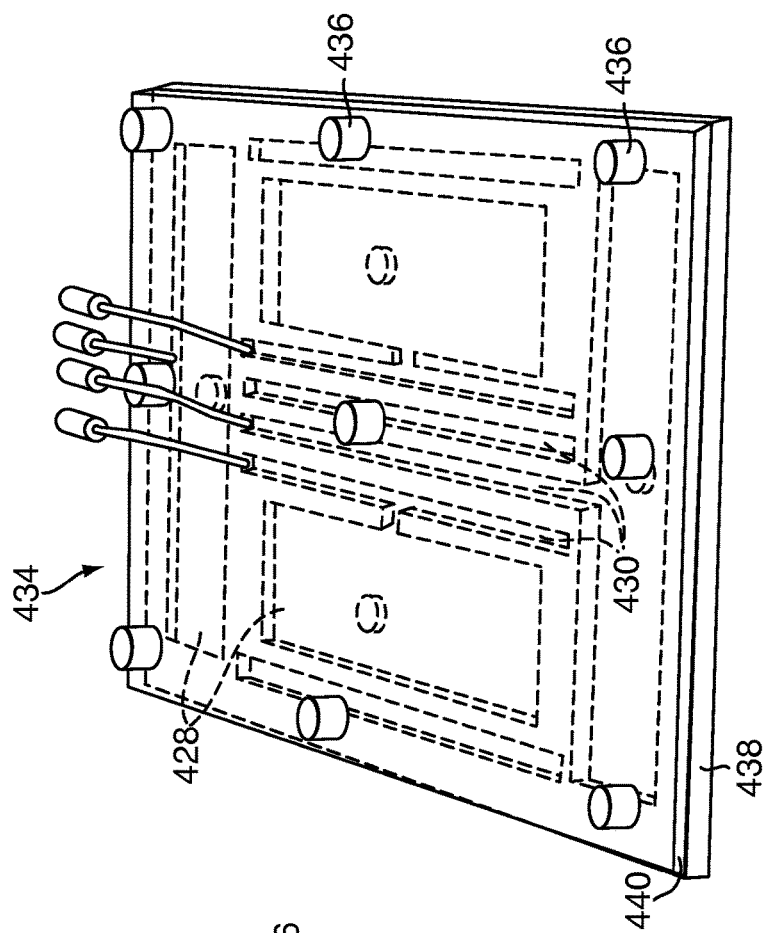
FIG. 13 is a bottom view of one embodiment of the dynamic interface of a dynamic support apparatus.
Figure 14:
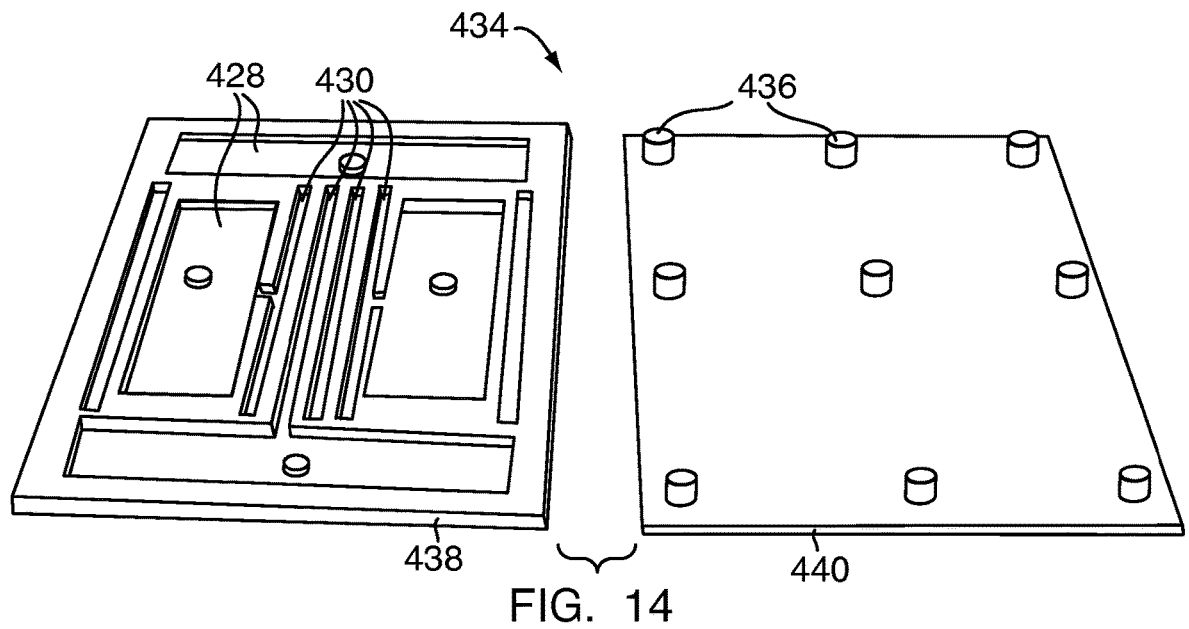
FIG. 14 is an exploded view of the dynamic interface of FIG. 13.

Referring to FIG. 13, the bladders 428 and fluid path connectors 430 may be molded as a part of the single integrated layer 434, such that the layer itself contains internal paths and compartments that serve as the fluid path connectors 430 and bladders 428, respectively. The molded single integrated layer 434 may also have nodules 436 to attach to a frame having corresponding apertures 437. As seen in FIG. 14, the single integrated layer 434 may be constructed by molding an actuation layer 438, containing the necessary bladders 428 and fluid path connectors 430, and a connection layer 440, containing nodules 436 for attaching the single integrated layer 434 to the frame. The actuation layer 438 and the connection layer 440 can then be bonded together to form the single integrated layer 434, as seen in FIG. 13. The molded single integrated layer 434 may be fabricated from any material that allows morphable chambers that can act as actuators of variable geometry. Such material may be silicon or rapid prototype molding material covered in a layer of silicon.

The dynamic interface 16 allows the support apparatus 10 to morph and adapt to the function of the residuum 12. For example, in an embodiment having actuators 24 that are bladders 28 filled with incompressible gas, when the residuum 12 morphs, possibly due to tissue volume variation or loading, the bladders 28 either inflate or deflate to adjust to the residuum 12 morphing and to maintain a secure and comfortable fit on the residuum 12.

The control system 18 controls the changing geometry of the actuators 24. The control system 18 may be hydraulic, pneumatic, electromechanical, mechanical, or any other actuator type mechanism that allows the actuators 24 to change geometry. In our exemplary embodiment, the bladders 28 are controlled by a pneumatic system and connected to the system by the fluid paths connectors 30.

Figure 15:
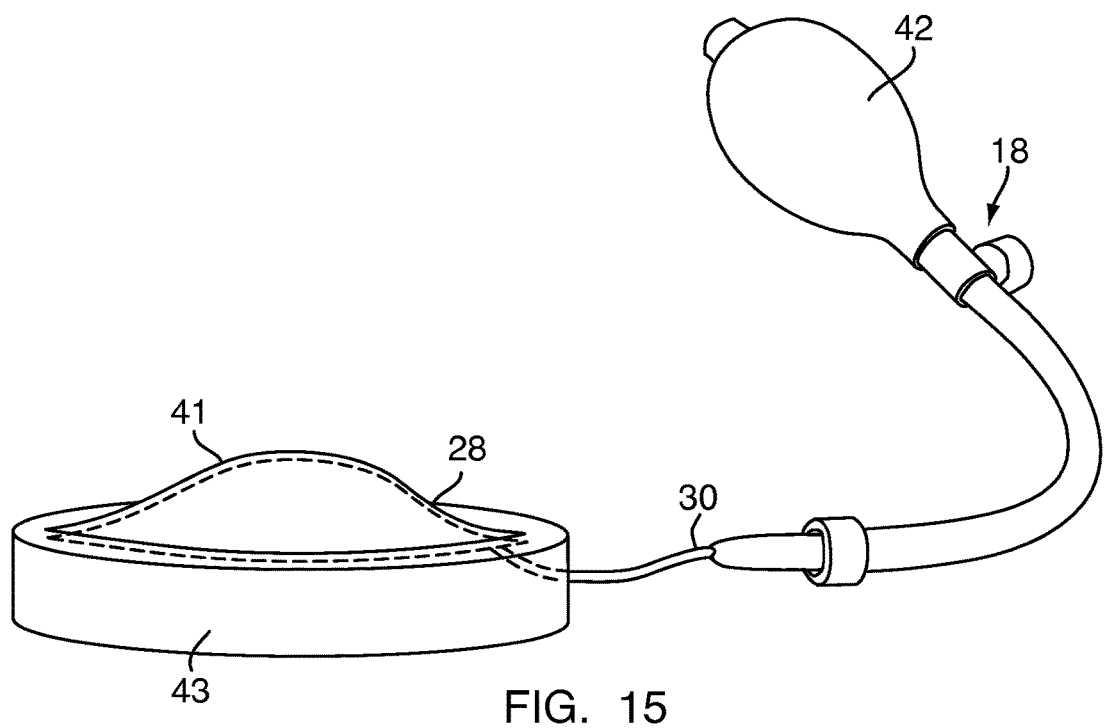
FIG. 15 is a perspective view of one embodiment of an actuator and control system of a dynamic support apparatus.

Referring now to FIG. 15, one embodiment of the control system 18 is shown as a manual system with a pressure bulb 42 that is connected to the bladder 28 by one or more fluid path connectors 30. When the user begins to feel instability or discomfort with the fit of the support apparatus 10, the user squeezes the pressure bulb 42, which can be set to either increase or decrease the air or liquid pressure in the bladder 28, thus adjusting the fit of the support apparatus 10 to the user's liking. If more than one bladder 28 is used, the user may be able to adjust the pressure in each individual bladder 28.

Still referring to FIG. 15, in this embodiment, the bladder 28 is laser welded. By laser welding a thin sheet 41 of bladder material to a substantially thicker sheet 43 of bladder material, the actuation can be isolated to a desired direction. As seen in FIG. 15, the bladder 28 deforms in the direction of the thin sheet 41 of material, while the remainder of the bladder 28 remains substantially unchanged.

Figure 16:
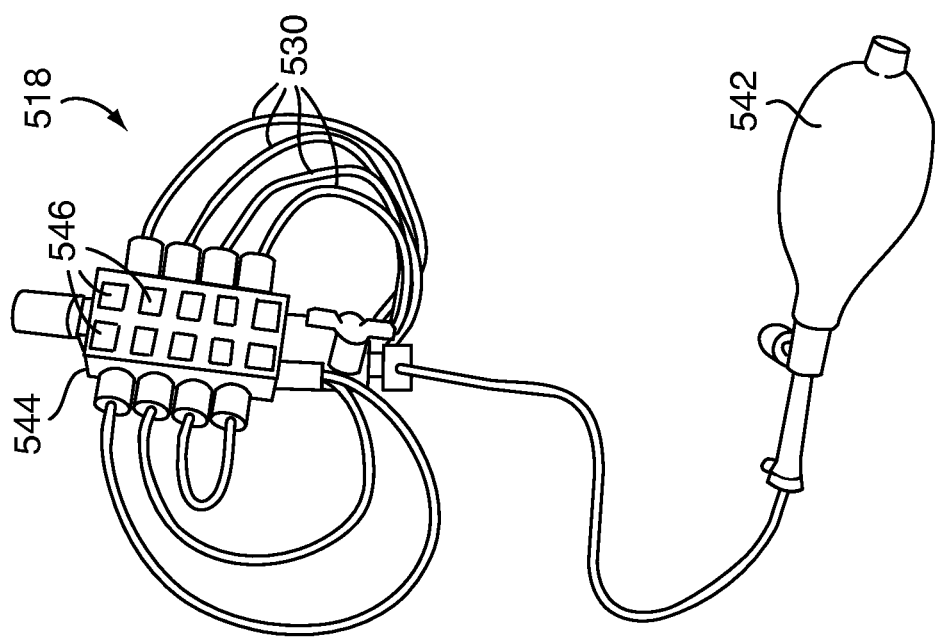
FIG. 16 is one embodiment of a manual control system of a dynamic support apparatus.

Referring now to FIG. 16, in an alternative embodiment of the control system 518, the pressure bulb 542 is connected to a plurality of bladders by one or more fluid path connectors 530 through a manifold 544. The manifold may have pressure selectors 546 allowing the user to adjust the pressure in the plurality of bladders by different amounts with the pressure bulb 542. The user may thus preset the pressure selectors 546 to provide optimal adjustment of the support apparatus. Additionally, the pressure selectors 546 also allow the user to target one or more specific bladder(s) of the plurality of bladders, such that pressure can be adjusted solely in the targeted bladder(s) while pressure in the rest of the plurality of bladders remains unchanged. This targeting capability permits pinpoint adjustment based on localized instability or discomfort.

Figure 17:
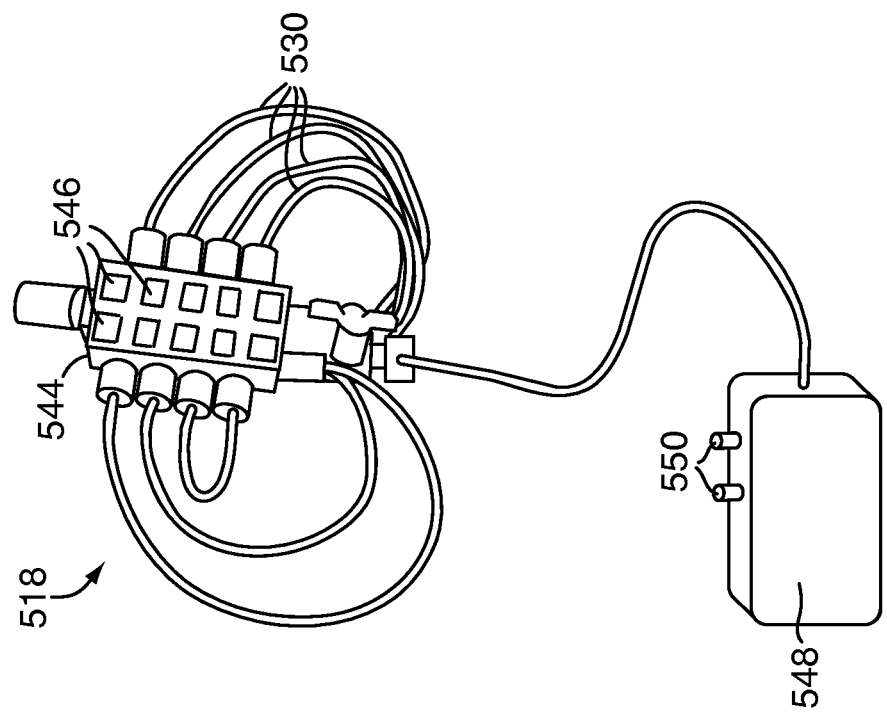
FIG. 17 is one embodiment of a manual control system of a dynamic support apparatus.

Referring now to FIG. 17, the control system 518 includes an electric pump 548 in place of the pressure bulb 542 for adjusting the pressure in the plurality of bladders. Pump control 550 allows the user to either increase or decrease the pressure in the bladders.

Figure 18:
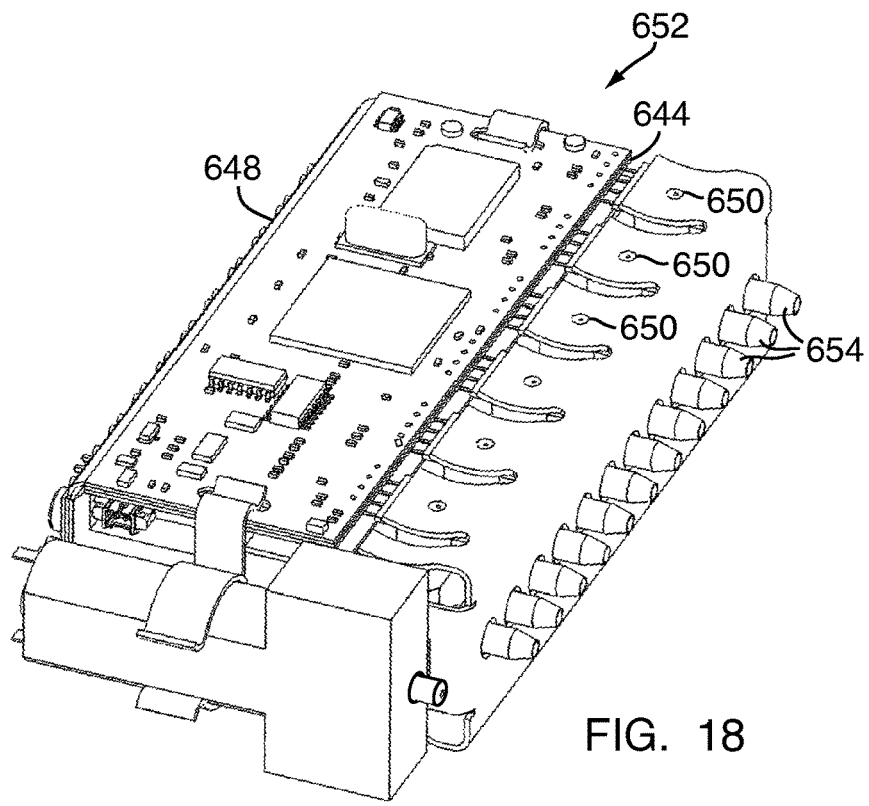
FIG. 18 is an internal perspective view of one embodiment of a control unit of a dynamic support apparatus.
Figure 19:
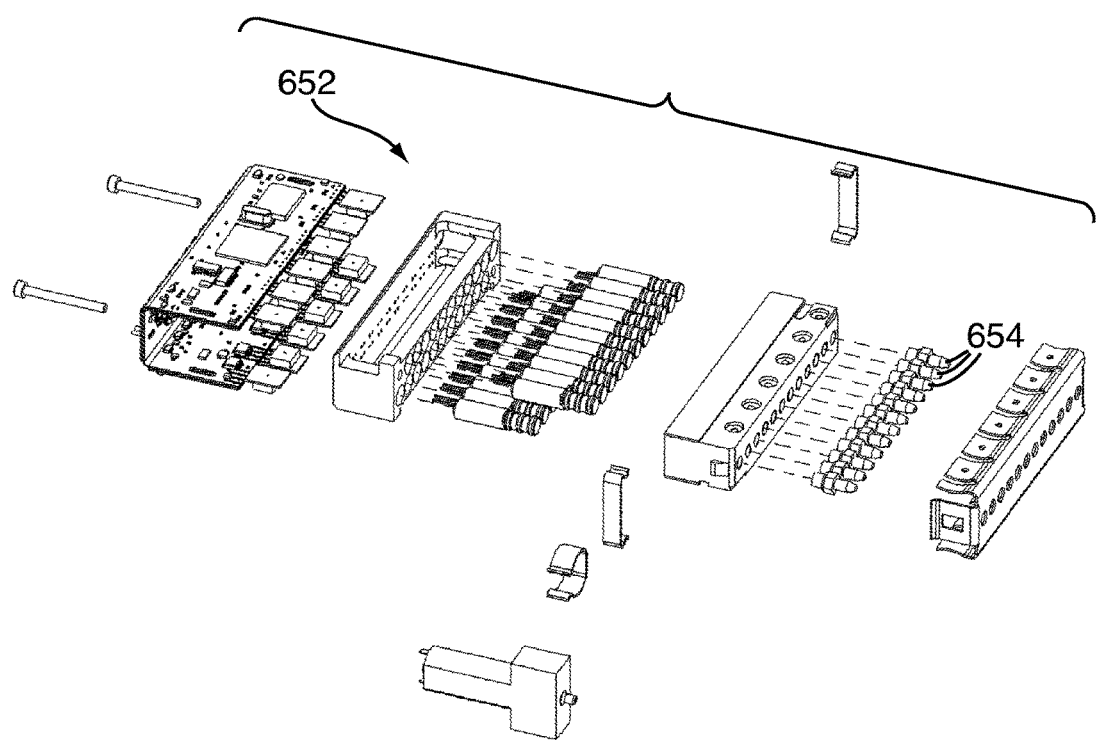
FIG. 19 is an exploded view of the control unit of FIG. 18.

Referring to FIGS. 18 and 19, an alternate embodiment incorporates the electric pump 648, the pump control 650, and the manifold 644 into a control unit 652. The fluid path connectors are attached to manifold outlets 654, allowing adjustment of each bladder using the pump control 650. The manifold 644, may be located in an accessible location, such as attached to the user's belt, or attached to the support apparatus itself.

Figure 20:
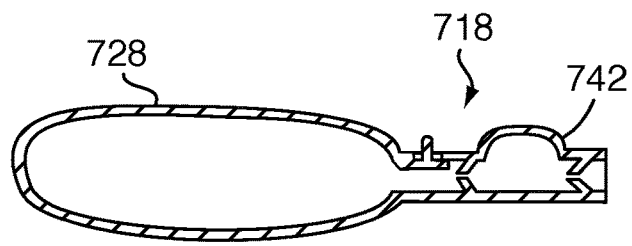
FIG. 20 is a cross-sectional view of one embodiment of an actuator and control system.
Figure 21:
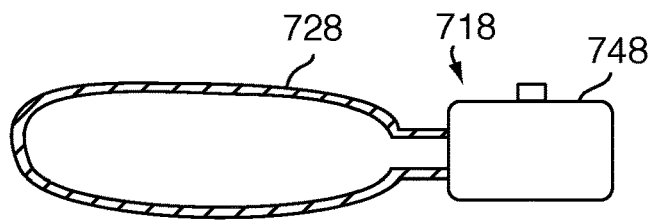
FIG. 21 is a cross-sectional view of one embodiment of an actuator and control system.

Referring now to FIGS. 20 and 21, an alternate embodiment integrates each bladder 728 and its control system 718. In the embodiment shown in FIG. 20, the control system 718 is a pressure bulb 742. In the embodiment shown in FIG. 21, the control system 718 is an electric pump 748. In such an embodiment, the patient would adjust the pressure of each bladder 728 by actuating its integrated control system 718.

The control system 18 may be an active control system that provides real-time adjustments in each actuator 24 to accommodate prosthetic load and user posture and to anticipate user needs. Referring back to FIGS. 18 and 19, with the exemplary embodiment having bladders 28 as actuators 24, the control unit 652 may include an active control system for activating the inflation/deflation of the bladders. The active control system may be in place of, or in addition to, the manual pump control 650. The active control system may have an input mechanism for gathering readings on the stability and fit of the support apparatus 10 with the residuum 12.

Figure 22:
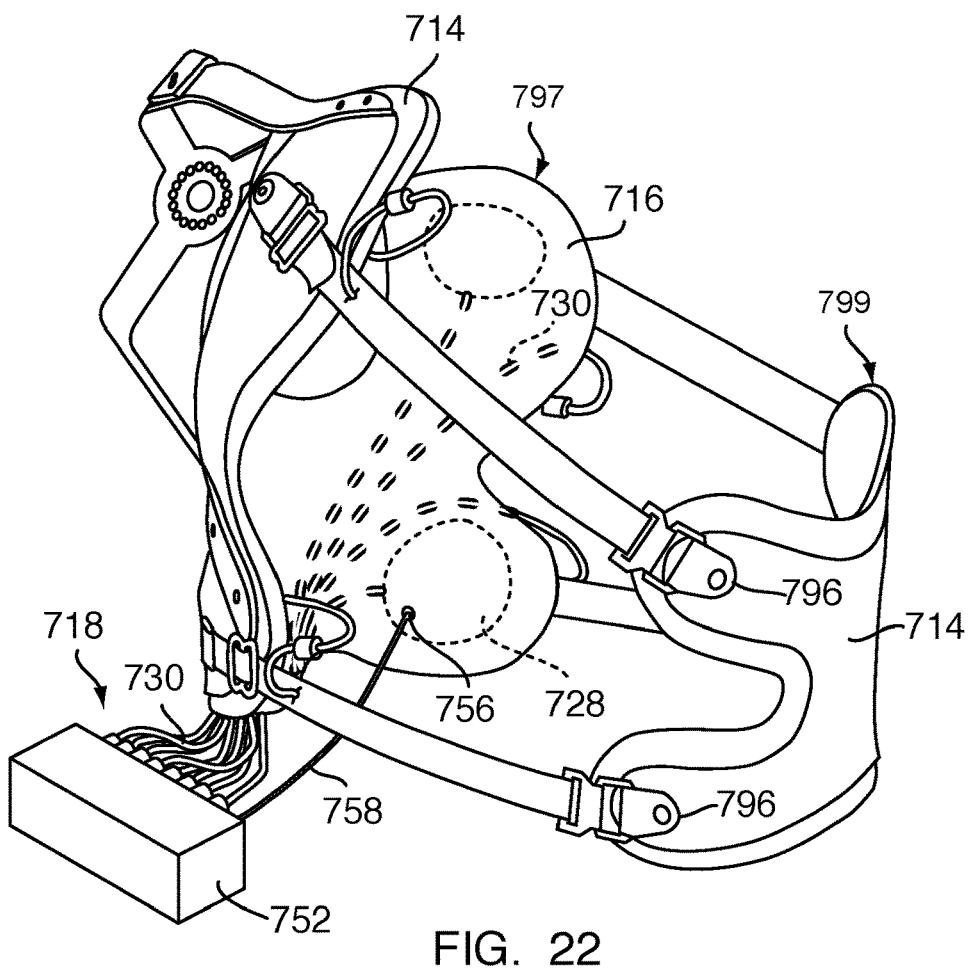
FIG. 22 is a perspective view of one embodiment of a dynamic support apparatus.

In some embodiments, the input mechanism includes sensors, such as pressure transducers, and feedback loops. The sensors may be placed on the inner shell of the frame, on the actuator(s), on the connector(s) connected to the actuator(s), or in any other suitable location, for providing information on the stability and fit of the support apparatus, as should be obvious to those skilled in the art. Controlled by a computer, the sensor(s) determine the pressure in the actuator(s) and, with the feedback loops, signals are sent to the control unit to either increase or decrease the actuator's pressure, possibly by inflation or deflation, thereby changing the volume of the actuator to exert the needed force to maintain the support apparatus's secure fit with the user's body. The computer for controlling the sensors is preferably integrated into the control unit of the control system 18. Referring to FIG. 22, with the exemplary embodiment having bladders 728 as actuators 724, a pressure sensor 756 may be placed on the bladder 728 to provide fit information to the control unit 752 through a sensor connector 758. In this embodiment, if a loose fit is detected by pressure sensor 756, i.e. the sensed pressure is low, a signal is sent to the control unit 752 to increase the pressure in the corresponding bladder 728 until a high pressure is sensed and therefore a stable condition is achieved. In this embodiment, the active control system adjusts the pressure of each actuator 724 in response to the part of the morphing residuum in contact with that actuator. This embodiment does not necessarily maintain a constant pressure in each bladder 728 nor does it necessarily maintain a total constant pressure against the residuum.

An alternative embodiment includes an active control system with sensors 756 and feedback loops that maintain constant pressure in each actuator 724. For example, in an embodiment having bladders 728, the sensors 756 and feedback loops may be placed on each bladder 728 or on each fluid path 730 of each bladder 728. The sensors 756 may be programmed to take an initial pressure reading of a bladder 728. The sensors 756 then take continuous pressure readings of the bladder 728, comparing these readings to the initial pressure. As the bladder pressure changes, the sensors 756 and feedback loops send signals to the control unit 752, which adjusts the pressure in the bladder 728 to maintain the initial bladder pressure. Maintaining a constant pressure in the bladders 728 can correspond to maintaining a constant fit between the support apparatus and the residuum.

Referring to FIGS. 23 and 24, the active control system may also include EMG electrodes 760 for providing control input to the control unit 752. The EMG electrodes 760 may be placed between the actuator(s) 724 and the skin of the residuum 712, on a separate layer or on each actuator 724. The EMG electrodes 760 sense voluntary underlying muscle activity and can be used to control some function of the prosthesis. In a support apparatus having bladders 728, the bladders 728 control the downward pressure of the EMG electrodes 760 on the skin of the residuum 712. This control of the downward force eliminates unintentional relative movement of the EMG electrodes 760, which generates an artifact signal, a common problem with EMG electrodes. As the residuum 712 morphs or the patient puts loads on the residuum 712, the pressure applied to each bladder 728 by the residuum 712 may vary, which in turn may vary the EMG electrodes' contact with the skin of the residuum 712. The pressure sensors sense this pressure differential, and the control unit may adjust the pressure of the bladder(s) 728 so as to put pressure back on the EMG electrodes 760. This pressure on the EMG electrodes 760 pushes the EMG electrodes 760 against the skin of the residuum 712, maintaining constant contact and a secure fit between the residuum and the support apparatus.

The control unit may include a partially-automatic control system for the actuator(s) 24 with preset actuator pressures. The user has a control unit 52 that can be programmed with preset numbers or modes that correspond to preset actuator pressures. These presets can be programmed by the patient while using the support apparatus 10 or can be pre-programmed. The preset pressures may be set to accommodate predefined support apparatus fits for a resting mode, a light load mode, a high load mode, a massage mode, or other types of activity. Depending on the patient's activity, the patient selects a number or mode on the control unit 52, which automatically adjusts the fit and pressure of the actuator(s) 24 to whatever pressure(s) was programmed to that number. The massage mode may be utilized to facilitate circulation in the residuum. For example, the controller may turn off one actuator 24 at a time to allow blood flow into the region of the turned off actuator 24. By cycling through the actuators one at a time, blood flow in the residuum 12 is assisted, without loss of stability of the dynamic support apparatus 10.

The temperature control mechanism 19 of the dynamic support apparatus 10 may include the apertures 20 of the support apparatus 10 in FIG. 2. The apertures 20 allow for cooling by ventilation, which reduces moisture and heat between the support apparatus 10 and the residuum 12. Additionally, the temperature control mechanism 19 may include ducted air flow over the skin of the residuum 12, heat exchangers, personal cooling systems (such as those found in Sharper Image's "Personal Cooling System"), ducted fans, or integrating sports or outdoor recreation clothing designed for heat/moisture management. The temperature control mechanism 19 may be placed in a separate layer between the dynamic interface 16 or top surface 22 and the residuum 12, integrated into the same layer as the dynamic interface 16, or integrated into the top surface 22 of the frame 14. An active control system, similar to the system already described, may also be used to control the temperature control mechanism 19 so as to maintain a constant temperature, through the use of temperature sensors, between the residuum 12 and the support apparatus 10.

Referring to FIG. 25, the temperature control mechanism 19 may include one or more duct(s) 64 connected to a plurality of orifices 66 and integrated into the dynamic interface 16. In this embodiment, temperature control is accomplished by supplying air through the duct(s) 64 and the plurality of orifices 66 to impinge on the skin of the residuum.

Figure 27:
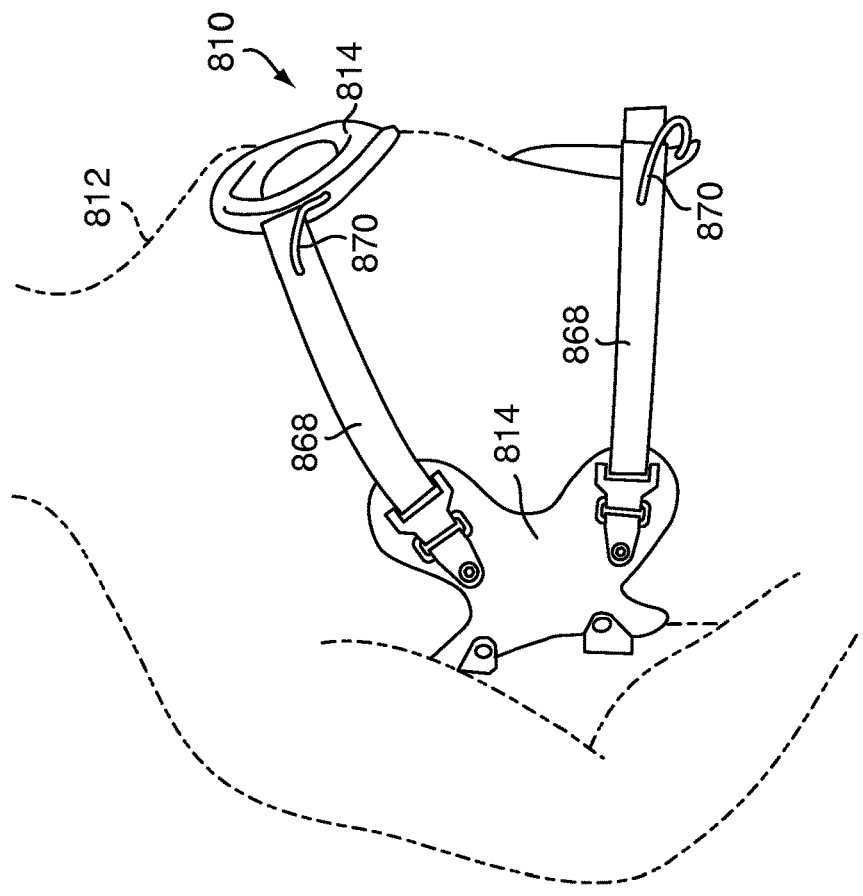
FIG. 27 is a side view of the dynamic support apparatus of FIG. 26.
Figure 26:
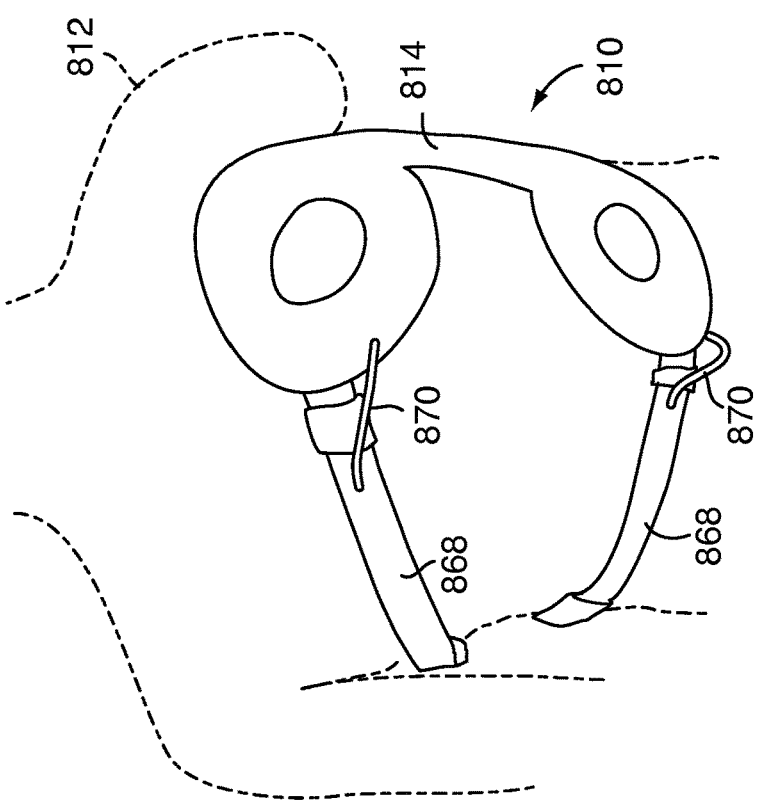
FIG. 26 is a front view of an alternative embodiment of a dynamic support apparatus as it is worn around the body.

While the exemplary embodiment described above relates to upper-limb prosthesis for TH amputees, the support apparatus can be used for transradial (TR) amputees and for shoulder disarticulation (SD) amputees. Referring now to FIGS. 26-28, one embodiment of a dynamic support apparatus 810 for SD amputees includes a frame 814, having actuators 824 and connectors 826, connected to one or more active straps 868, such as McKibben artificial muscles. Each active strap 868 contains at least one actuator and at least one strap connector 870 for connecting the actuator to the control system. Similar to those embodiments already described, each active strap 868 may also contain sensors and feedback loops for providing fit information to the control system. The active straps are connected to the control system and control unit. Thus, as pressure and tension on the active strap(s) 868 change due to load variations on the residuum 812, the sensors signal the control unit to adjust the pressure of the strap(s)'s actuator(s), which in turn adjusts the tension and length of the strap. These adjustments ensure a secure fit against the user's body and ensure stability of the prosthesis. The active straps 868 and strap connectors 870 may be integrated with the dynamic interface 816, such that one control system controls both the dynamic interface 816 and the active straps 868 simultaneously. As should be understood by those skilled in the art, the strap connectors 870 may alternatively be routed to a separate control unit specifically for the active straps 868.

Referring to FIG. 28, in addition to controlling the tension and length of active straps 868 by actuators, each active strap 868 may additionally contain a length adjuster 872, which may be used to manually adjust the length and fit of each active strap 868.

Referring to FIGS. 29 and 30, in the exemplary embodiment having bladders 828 for actuators 824 and fluid path connectors 830 for strap connectors 870, the bladder 828 is encased in a deformable strap material 874, such as nylon webbing. The bladder 828 is connected to the control system by the fluid path connector 830. The end of each active strap 868 has an attachment mechanism 876 for attaching the active strap 868 to the frame. The active strap 868 is in a preset condition in FIGS. 29 and 30, having a strap length 878 and a preset bladder cross-section.

Referring to FIGS. 31 and 32, the active strap 868 is in an actuated condition having an actuated bladder cross section and an actuated strap length 880 that is less than the preset strap length shown in FIG. 29. Accordingly, when instability is detected in the support apparatus, either by the control system or by the user, pressure may be increased in the active strap 868, causing the bladder 828 to expand from the preset condition of FIGS. 29 and 30 to the actuated condition of FIGS. 31 and 32. As pressure increases in the bladder 828, the deformable strap material 874 deforms, decreasing the length of the active strap 868 and increasing stability in the support apparatus.

Figure 33:
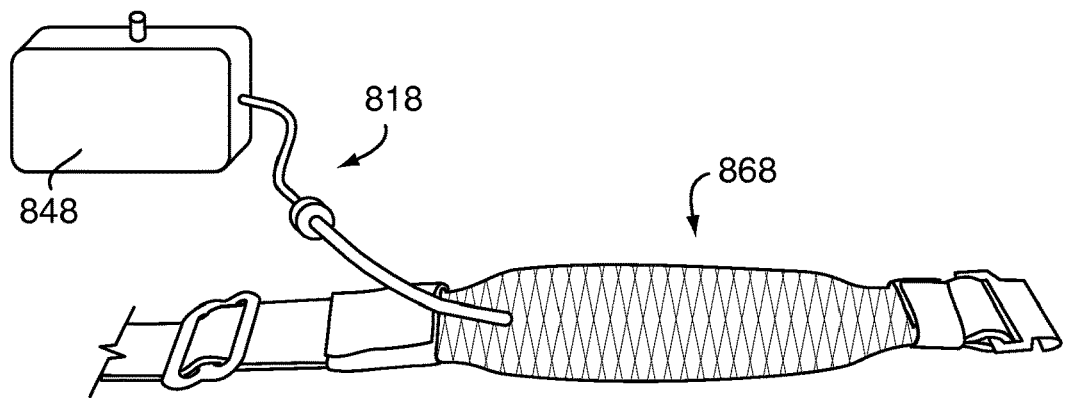
FIG. 33 is a perspective view of one embodiment of an active strap and control system of a dynamic support apparatus.
Figure 34:
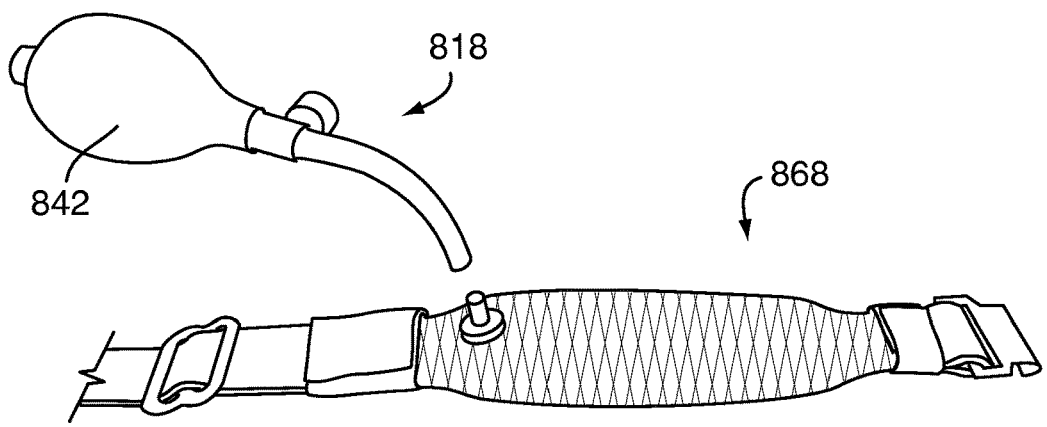
FIG. 34 is a perspective view of an alternative embodiment of an active strap and control system of a dynamic support apparatus.

Referring to FIG. 33, the control system 818 of each active strap 868 may be an electric pump 848, such that the pressure in each active strap 868 may be adjusted independent of the other active straps 868 and the dynamic interface. Referring to FIG. 34, the control system 818 of each active strap 868 may alternatively be a pressure bulb 842, such that the pressure in each active strap 868 may be adjusted independent of the other active straps 868 and the dynamic interface. Although shown as separate units in FIGS. 33 and 34, the control system 818 may be integrated with the bladder 828 similar to that shown in FIGS. 20 and 21.

Unlike typical McKibben artificial muscles, which are used in high-pressure applications, the active straps 868 in the dynamic support apparatus 810 are operated under low-pressure conditions. Accordingly, various configuration changes have been made to the inflation, arrangement and strap characteristics of the active straps 868 to increase performance and efficiency in low-pressure conditions. The actuator length to strap length for the active strap 868 is about two-thirds the length seen in the prior art. This increases actuation with less pressure, and makes the active strap 868 and the support apparatus more responsive. Additionally, when the actuator in active strap 868 is a bladder 828, it may be fabricated wider than the strap itself so that the bladder 828 can be inflated, causing the strap diameter to increase, without putting energy into stretching the bladder 828 itself. Bladders that are fabricated by laser welding, such as the bladder 28 shown in FIG. 15, also provide for improved performance in low-pressure conditions because they can be constructed to deform the active strap 868 in specific shapes and locations, rather than only circular deformation.

Figure 35:
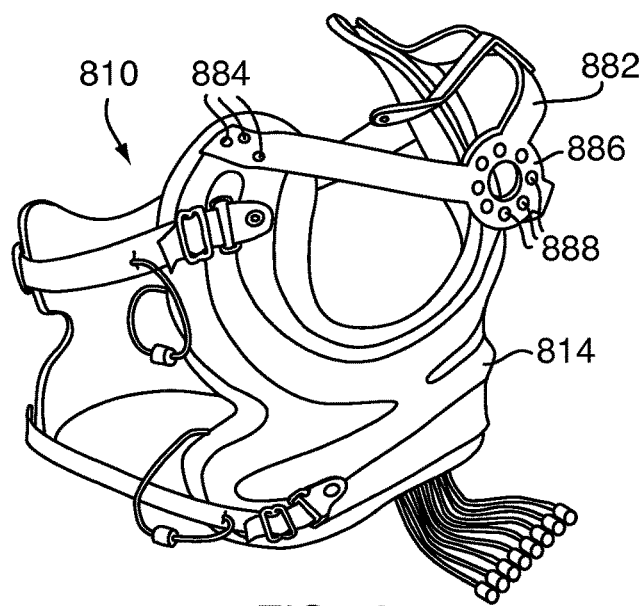
FIG. 35 is a front perspective view of one embodiment of a dynamic support apparatus showing a prosthetic interface.
Figure 38:
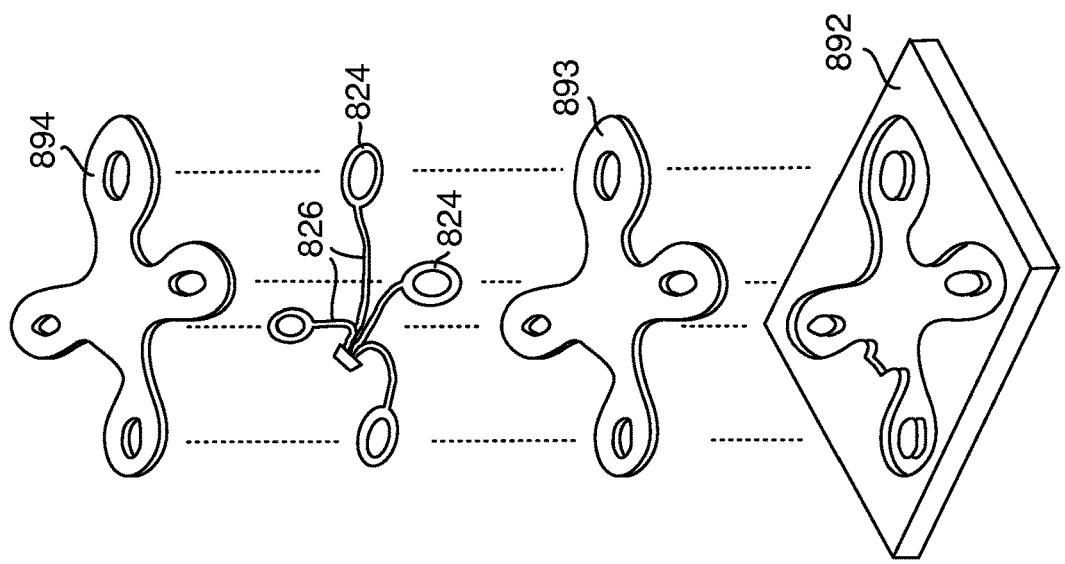
FIG. 38 is an illustration of a portion of the technique for fabricating and embodiment of a dynamic interface for a dynamic support apparatus.
Figure 37:
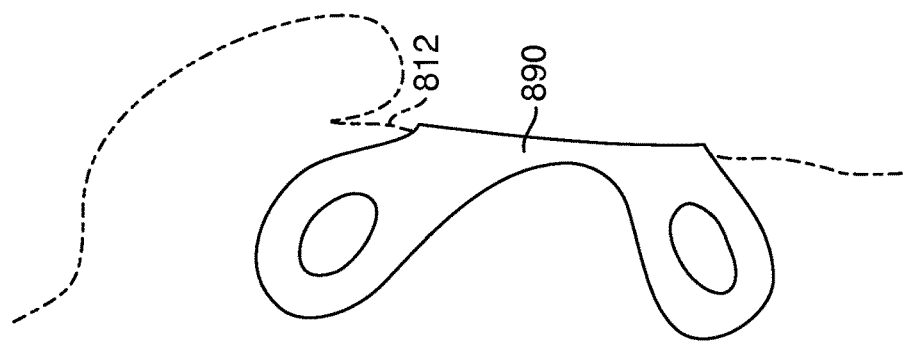
FIG. 37 is an illustration of a portion of one technique for fabricating and embodiment of a dynamic interface for a dynamic support apparatus.
Figure 36:
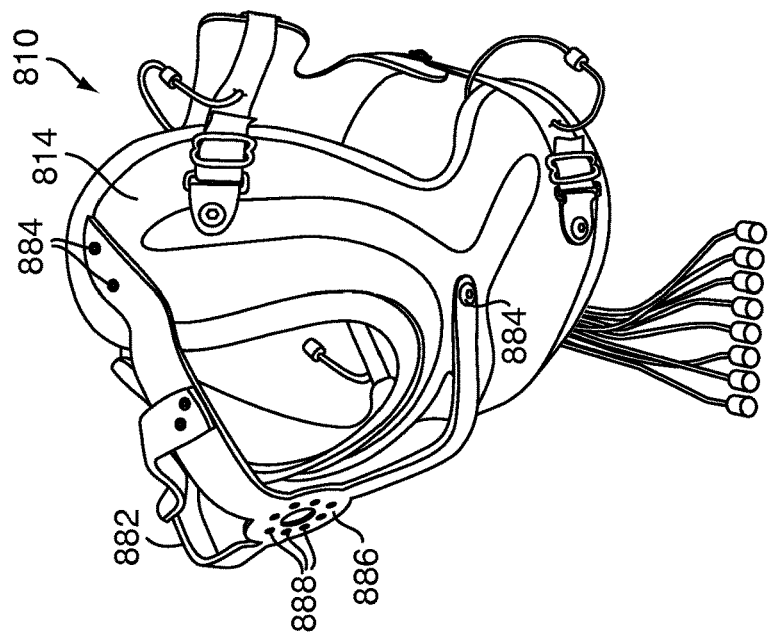
FIG. 36 is a rear perspective view of the dynamic support apparatus of FIG. 35.
Figure 40:
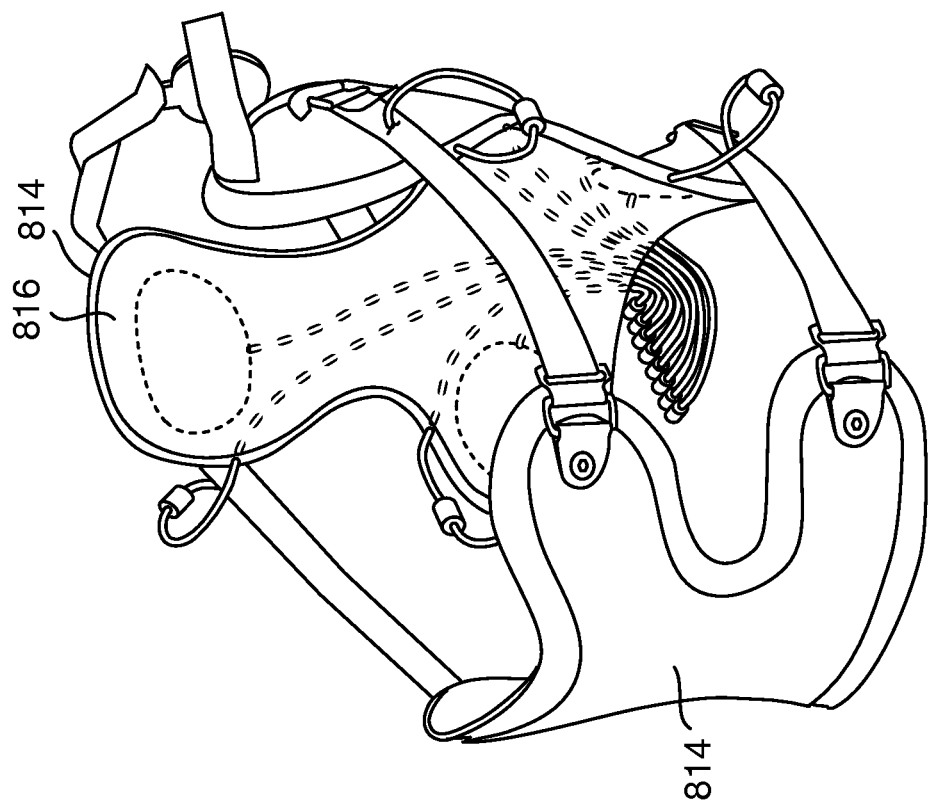
FIG. 40 is a front perspective view of the dynamic support apparatus of FIGS. 37-39.
Figure 39:
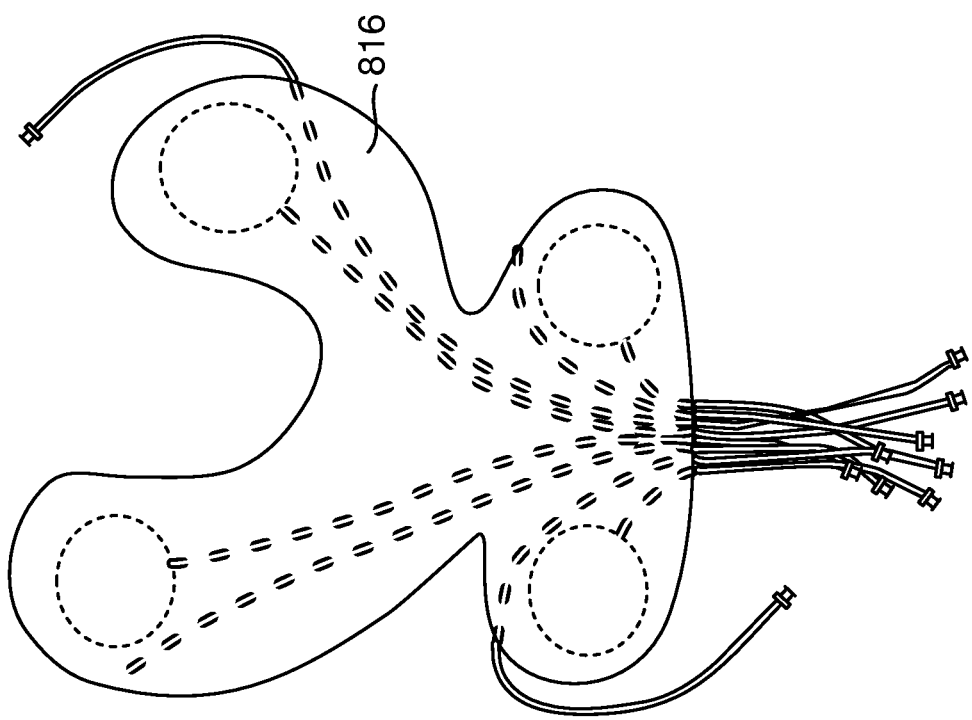
FIG. 39 is a front view of the dynamic interface fabricated from the technique of FIGS. 37 and 38.
Figure 42:
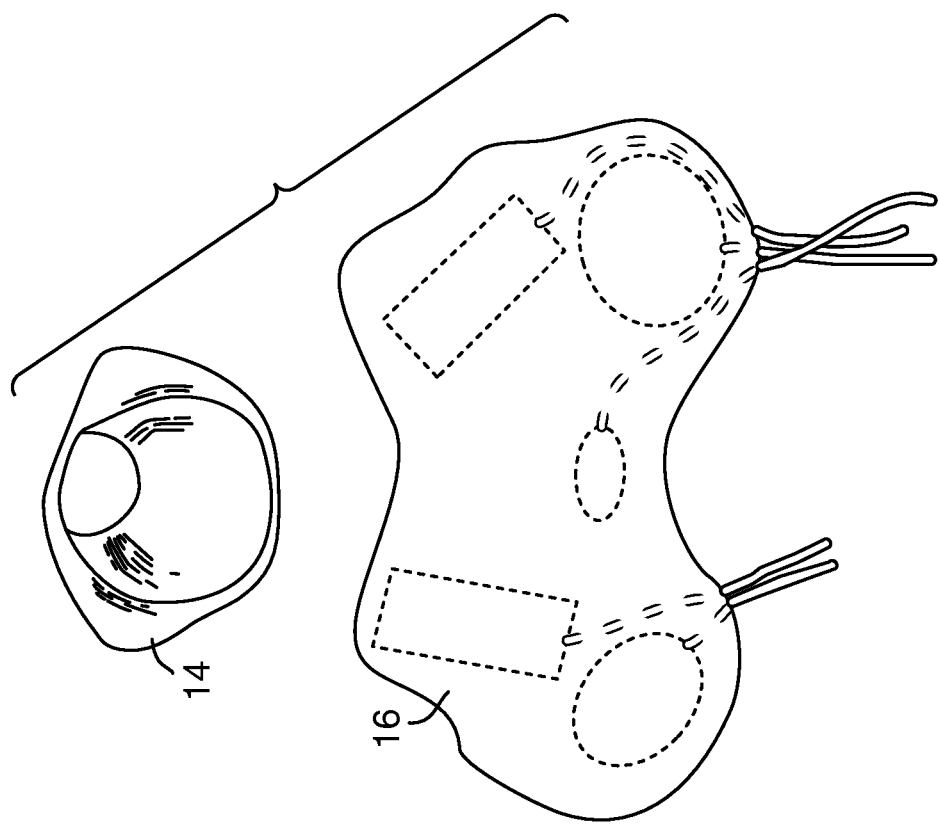
FIG. 42 is a front view of an alternative embodiment of a dynamic interface fabricated from the technique of FIGS. 37 and 38.
Figure 41:
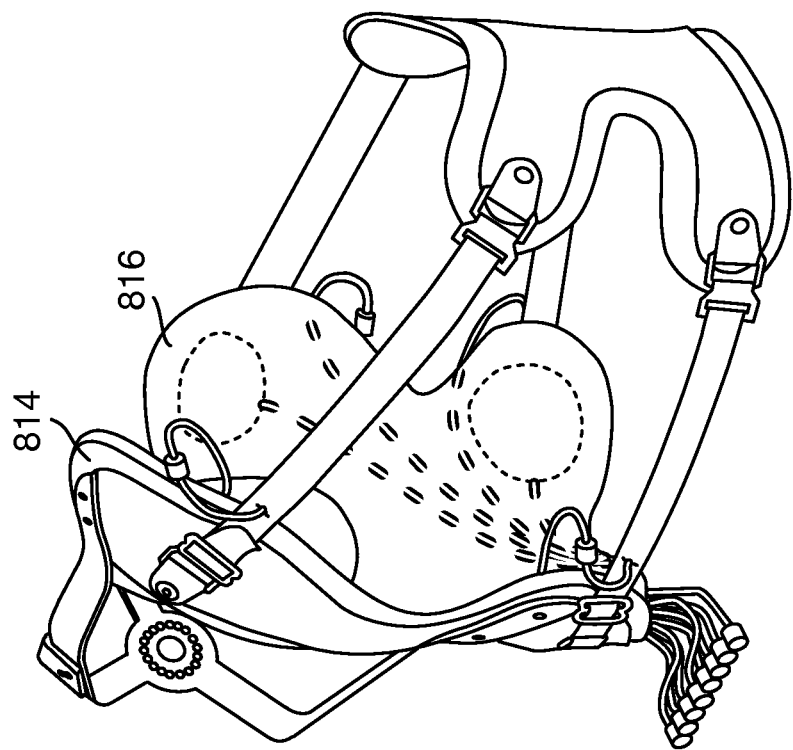
FIG. 41 is a rear perspective view of the dynamic support apparatus of FIGS. 37-39.
Figure 46:
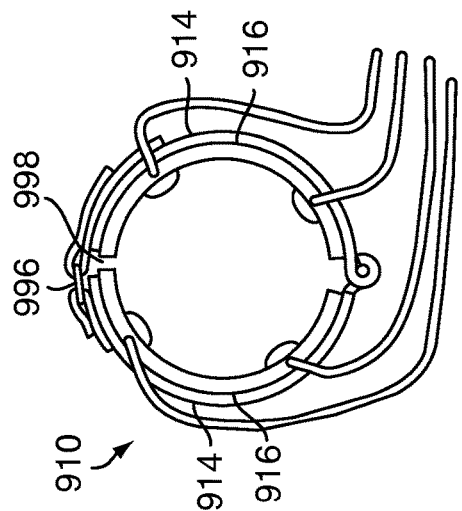
FIG. 46 is a top view of an alternative embodiment of a dynamic support apparatus.
Figure 47:
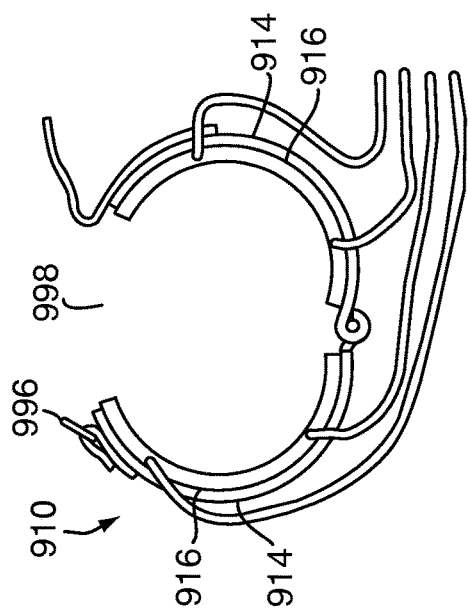
FIG. 47 is the dynamic support apparatus of FIG. 46 when partially opened.
Figure 43:
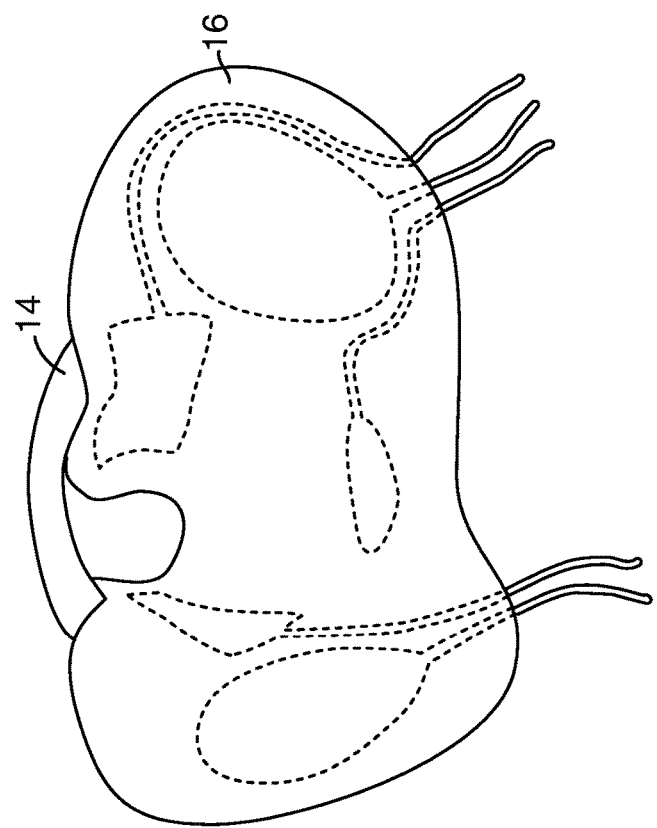
FIG. 43 is a front assembled view of the dynamic interface of FIG. 42.
Figure 45:
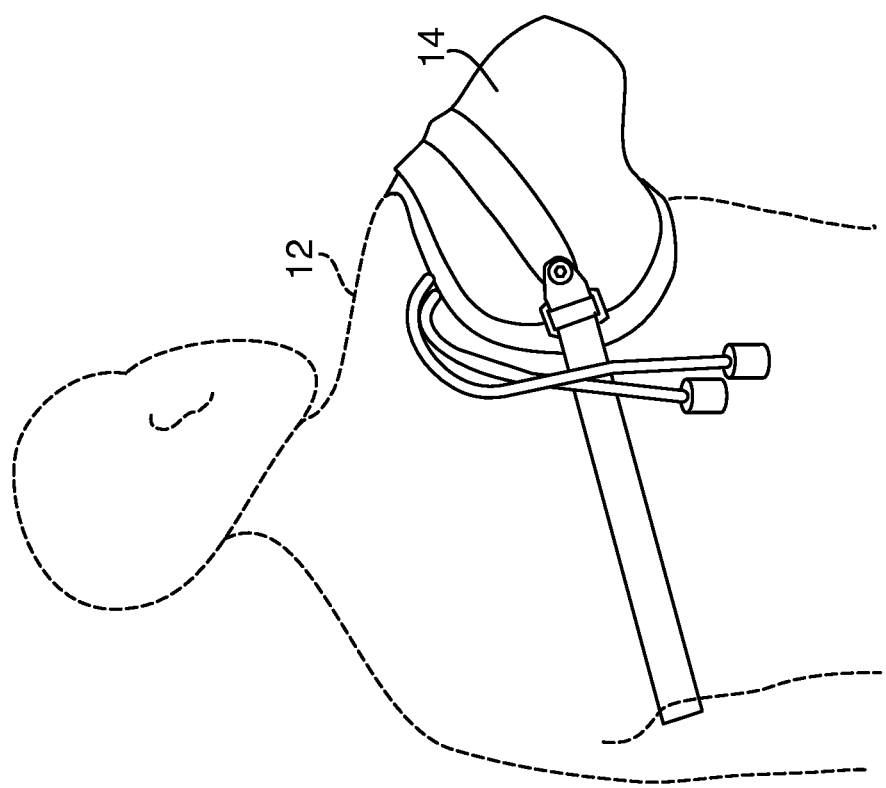
FIG. 45 is a rear perspective view of the dynamic support apparatus of FIG. 43 as worn by a patient.
Figure 44:
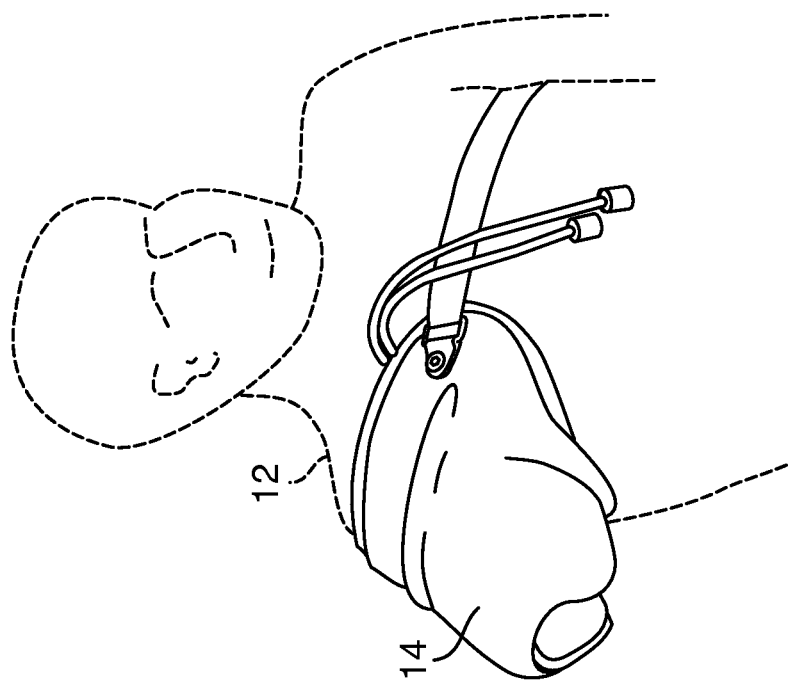
FIG. 44 is a front perspective view of the dynamic support apparatus of FIG. 43 as worn by a patient.
Figure 48:
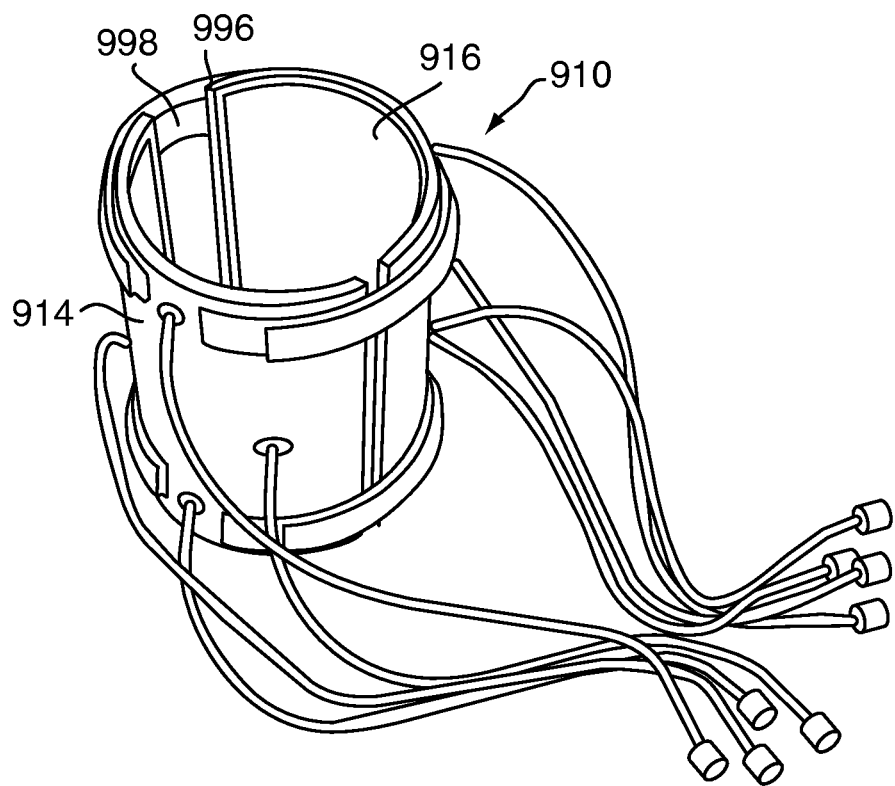
FIG. 48 is a perspective view of the dynamic support apparatus of FIG. 46.
Figure 49:
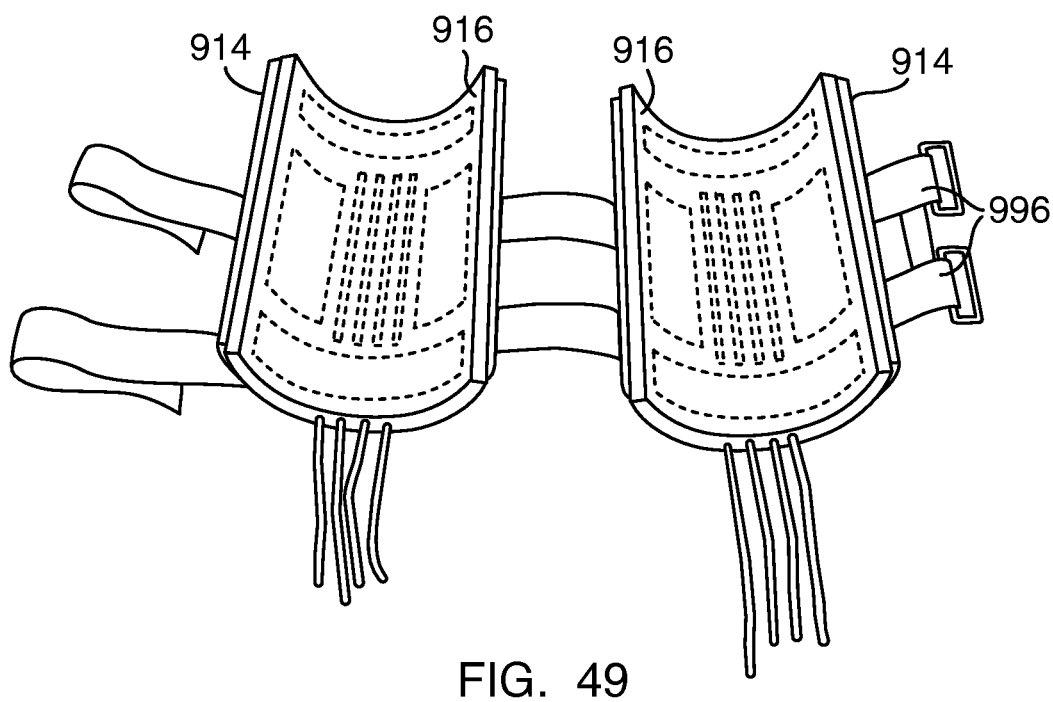
FIG. 49 is a side view of the dynamic support apparatus of FIG. 46 when completely opened.

Referring to the embodiment shown in FIGS. 35 and 36, attached to the support apparatus 810 is a prosthetic interface 882 for attaching a prosthesis (not shown) to the support apparatus 810. The prosthetic interface 882 is fixedly attached to the support apparatus 810 by attachment means 884, which may be rivets, bolts or any similar means of attachment. The prosthetic interface 882 has a prosthetic mount 886 for to which the prosthesis may be attached. The prosthetic mount 886 preferably includes a standard coupling configuration to facilitate attachment of the prosthesis. Although shown as holes 888, it should be understood that the standard coupling configuration could also be a bolt configuration that interfaces with corresponding holes on the prosthesis. The prosthetic interface 882 should be rigid in construction, such that it does not bend or flex when the attached prosthesis is used to lift a heavy object.

Referring to FIGS. 37-41, a method of fabricating the dynamic interface of the dynamic support apparatus may be a layer molding technique. For example, for the SD prosthesis support apparatus 810, such method may involve the steps of scanning the contour of a patient's residuum 812 in an outline 890 where the frame will sit on the residuum 812; flattening the scanned contour so that it can be made into a template for a mold 892; machining the "flattened" template into the mold 892; pouring silicone or similar material in the mold 892 to half the final thickness of the dynamic interface 816 to create a first interface layer 893; laying the actuator(s) 824 and connector(s) 826 on top of the first interface layer 893; pouring silicon or similar material on top of the actuator(s) 824 and connector(s) 826 to a desired thickness of the dynamic interface 816 to create a second interface layer 894; removing the resulting dynamic interface 816 from the mold 892; and connecting the resulting dynamic interface 816 to a control system (not shown) and a frame 814.

Although described with regard to the SD prosthesis support 810, as seen in FIGS. 42-45, the dynamic interface 16 fabricated by the layer molding technique described above can also be applied to other types of prosthesis support apparatuses by scanning the appropriate part of the residuum 12 and attaching the resulting dynamic interface 16 to the frame 14 and control system.

An alternative method of fabricating a dynamic interface, for example for a TH prosthesis support apparatus, may involve the steps of scanning the contour of a patient's residuum to form an inner mold of the TH residuum; forming the inner mold of the TH residuum; coating the inner mold with an inner layer of liner made of material such as silicon or similar material; scanning the inner mold to generate an outer mold; forming an outer mold; laying the actuator(s) 24 and connector(s) 26 on top of the inner layer of liner; pouring an outer layer of silicon or similar material on top of the inner layer, the actuator(s) 24, and the connector(s) 26; using the outer mold to form the outer layer of the dynamic interface 16; and connecting the resulting dynamic interface 16 to a control system 18 and a frame 14.

Referring back to FIG. 22, the frame 714 may be capable of expanding or opening to facilitate donning and doffing the support apparatus. One or more securing mechanisms 796, such as snaps or latches, may connect a first portion 797 of the dynamic support apparatus to a second portion 799 of the dynamic support apparatus and may be used to prevent expansion or opening of the frame 714 while the support apparatus 710 is being worn by the user.

Referring to FIGS. 46-49, in an alternative embodiment, the support apparatus 910 may be capable of expanding or opening parallel to its longitudinal axis to facilitate donning and doffing. An opening 998 of the frame 914 may run along only a portion of the length of the support apparatus 910 or may run along the entire length of the support apparatus 910 from the proximal to the distal end of the apparatus. The securing mechanism 996, such as a circumferential straps, may be used to prevent expansion or opening of the frame while the support apparatus is being worn by the user. In this embodiment, the dynamic interface 916 may be composed of multiple portions, each being attached to a part of the frame 914.

Some embodiments may also include an exhaust system that is incorporated into the control system. The exhaust system may channel excess fluid resulting from the release of pressure in the actuators to one or more exhaust outlets. In the exemplary embodiment, with air as the fluid, the exhaust outlets may vent the air into the atmosphere. In other embodiments, the exhaust outlets may channel the air into a reservoir, from which the fluid can be drawn back into the system to increase pressure. These exhaust outlets may also be strategically positioned or ducted along the frame to channel flow over the surface of the residuum. This flow could aid convective cooling of the residuum.

The dynamic interface is able to change geometry to provide a fit with the residuum 12. The user may manually actuate the dynamic interface to increase stability as needed. The dynamic support apparatus 10 may include a temperature control system to increase the comfort of the dynamic support apparatus. The frame may be capable of opening to assist the user in donning and doffing the dynamic support apparatus.

The control system may actively actuate the dynamic interface based on fit information provided by sensors. The control system may include preset modes defining predefined apparatus fits, such that the fit may be changed for each mode. The control system may include a massage mode for increasing blood circulation in the residuum.

Although the dynamic support apparatus is illustrated for use with an upper-limb prosthesis, the support apparatus is adaptable to other body appliances such as ski boots, shoes, backpacks, lower-limb prostheses, braces worn around a body part, or anything designed to be worn around a body part.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. A dynamic support apparatus for use with a prosthetic device, the dynamic support apparatus comprising:
   a frame having a surface;
   a dynamic interface, capable of changing its geometry, disposed on the surface of the frame, the dynamic interface having a plurality of actuators that are bladders capable of changing geometry when filled with a gas or a liquid; and
   a control system operably connected to the dynamic interface by at least one connector through a manifold that controls the distribution of the gas or the liquid to the bladders;
   wherein the control system is configured to supply the gas or liquid to the manifold for distribution to the bladders;
   wherein the control system is an active control system including a computer programmed with a plurality of user-selectable preset modes that automatically adjust the gas or liquid supplied by the control system, each user-selectable preset mode being user-selectable in the control system and defining different preset pressures for the bladders, the different preset pressures providing a different predefined apparatus fit suited for a different type of user activity, the different predefined apparatus fit being based on the total gas or liquid supplied by the control system and the user-adjustable pressure selectors; and
   wherein, upon a change in a selected user-selectable preset mode from a first selected user-selectable preset mode of the plurality of user-selectable preset modes to a second selected user-selectable preset mode of the plurality of user-selectable preset modes, the control system automatically adjusts the gas or liquid supplied to the bladders to change the bladders to the different preset pressures defined by the second selected user-selectable preset mode from the different preset pressures defined by the first selected user-selectable preset mode in order to change a fit of the apparatus from a first predefined apparatus fit for a first type of user activity to a second predefined apparatus fit for a second type of user activity.

2. The dynamic support apparatus according to claim 1, wherein each bladder of said bladders is capable of changing geometry in only a specific direction, and is not capable of changing geometry in directions other than the specific direction.

3. The dynamic support apparatus according to claim 1, wherein the control system has at least one electric pump.

4. The dynamic support apparatus according to claim 1, wherein the control system has at least one sensor for providing information of a stability and fit of the support apparatus to the computer of the control system.

5. The dynamic support apparatus according to claim 4, wherein the at least one sensor is a pressure transducer and the information of the stability and fit of the support apparatus is pressure measured by the pressure transducer.

6. The dynamic support apparatus according to claim 5, wherein, in at least one mode of the plurality of user-selectable preset modes, the control system is configured to monitor the pressure measured by the pressure transducer and to supply the gas or liquid so that the pressure measured by the pressure transducer remains at a constant pressure, the constant pressure being defined by one of the different preset pressures for the at least one mode.

7. The dynamic support apparatus according to claim 4, wherein the control system actuates a change in the geometry of the dynamic interface based on the information provided by the at least one sensor.

8. The dynamic support apparatus according to claim 1, wherein the plurality of actuators and the connector are molded inside the dynamic interface.

9. The dynamic support apparatus according to claim 1, wherein plurality of actuators and the connector are integrally molded as a part of the dynamic interface.

10. The dynamic support apparatus according to claim 1, wherein the frame has an opening configured to allow a first portion of the dynamic support apparatus to expand relative to a second portion of the dynamic support apparatus to facilitate donning and doffing of the dynamic support apparatus.

11. The dynamic support apparatus according to claim 10, wherein the dynamic support apparatus has a securing mechanism to preclude expansion thereof.

\* \* \* \* \*